(12) United States Patent
Kishkovich et al.

(10) Patent No.: US 6,855,557 B2
(45) Date of Patent: Feb. 15, 2005

(54) DETECTION OF BASE CONTAMINANTS IN GAS SAMPLES

(75) Inventors: Oleg P. Kishkovich, Greenville, RI (US); William M. Goodwin, Medway, MA (US)

(73) Assignee: Extraction Systems, Inc., Franklin, MA (US)

( * ) Notice: Subject to any disclaimer, the term of this patent is extended or adjusted under 35 U.S.C. 154(b) by 0 days.

(21) Appl. No.: 09/783,232

(22) Filed: Feb. 14, 2001

(65) Prior Publication Data

US 2001/0019844 A1 Sep. 6, 2001

Related U.S. Application Data

(62) Division of application No. 09/232,199, filed on Jan. 14, 1999, now Pat. No. 6,207,460.

(51) Int. Cl.$^7$ .................. G01N 31/12; G01N 21/00; G01N 35/08; G01N 37/00; G01N 33/00

(52) U.S. Cl. .................. 436/106; 436/75; 436/111; 436/116; 436/52; 436/56; 422/80; 422/94; 422/62

(58) Field of Search .................. 422/94, 62, 80, 422/93, 58, 116, 91; 436/52, 56, 75, 116, 111, 106, 180, 113, 172; 261/23.1; 96/413, 376

(56) References Cited

U.S. PATENT DOCUMENTS

| 35,234 A | 5/1862 | Harris et al. .................. 55/233 |
| 3,620,931 A | 11/1971 | Reichner et al. ............ 204/1 T |
| 3,647,387 A | 3/1972 | Benson et al. ............ 23/232 R |

(List continued on next page.)

FOREIGN PATENT DOCUMENTS

| CA | 120 1646 | 3/1986 |
| DE | 214213 | 10/1984 |
| JP | 5-8085155 | 5/1983 |
| JP | 63-24149 | 5/1986 |
| JP | 4-50756 | 2/1992 |
| JP | 5-45289 | 2/1993 |
| JP | 4-315048 | 3/1993 |
| JP | 5-302895 | 11/1993 |
| JP | 6-118077 | 4/1994 |
| WO | 92/10749 | 6/1992 |
| WO | 98/38508 | 9/1998 |

OTHER PUBLICATIONS

Viewgraph, "Compact Chemiluminescent NO/NO$_x$ Stack Gas Analyzer," Instrumatic International, Received by One of the Inventors on Nov. 21, 1997.

Thermo Environmental Instruments Inc., Model 17 Chemiluminescence NH$_3$ Analyzer Instruction Manual (1994).

*Primary Examiner*—Jill Warden
*Assistant Examiner*—Brian R. Gordon
(74) *Attorney, Agent, or Firm*—Weingarten, Schurgin, Gagnebin & Lebovici LLP

(57) ABSTRACT

A detection system for detecting contaminant gases includes a converter, a detector, a primary channel for delivering a target gas sample through the converter to the detector, and at least two scrubbing channels for delivering a reference gas sample through the converter to the detector. Each of the scrubbing channels includes a scrubber for removing basic nitrogen compounds from the reference gas sample, while the primary channel preferably transmits the target gas sample without scrubbing. The converter converts gaseous nitrogen compounds in the target gas sample to an indicator gas, such as nitric oxide (NO), and a control system directs the flow of a gas sample among the primary channel and the scrubbing channels. In accordance with one aspect of the invention, the basic-nitrogen-compound concentration can be measured by comparing the concentration of the indicator gas detected in the reference sample with the detected indicator-gas concentration in the target sample. The use of multiple scrubbing channels enables the detection to operate continuously since each scrubber can be alternately purged while another is scrubbing.

20 Claims, 13 Drawing Sheets

U.S. PATENT DOCUMENTS

| | | | | |
|---|---|---|---|---|
| 3,727,029 | A | 4/1973 | Chrow | 219/301 |
| 3,787,184 | A | 1/1974 | Novak et al. | 23/230 R |
| 3,807,233 | A | 4/1974 | Crawford | 73/421 |
| 3,851,493 | A | 12/1974 | Gifford et al. | 62/13 |
| 3,904,371 | A | 9/1975 | Neti et al. | 23/232 R |
| 3,911,413 | A | 10/1975 | Wallace | 340/237 R |
| 3,919,397 | A | 11/1975 | Gould | 423/405 |
| 3,964,889 | A | 6/1976 | Lachnit | 55/429 |
| 3,967,933 | A | 7/1976 | Etess et al. | 23/232 |
| 3,969,479 | A | 7/1976 | Lonnes et al. | 423/210 |
| 3,984,313 | A | 10/1976 | Higgins | 210/26 |
| 3,996,008 | A | 12/1976 | Fine et al. | 23/254 R |
| 4,033,117 | A | 7/1977 | Smith | 60/39.46 S |
| 4,049,383 | A | 9/1977 | Burton et al. | 23/232 |
| 4,059,409 | A | 11/1977 | Barto et al. | 23/284 |
| 4,070,155 | A | 1/1978 | Fraim | 23/230 PC |
| 4,154,586 | A | 5/1979 | Jones et al. | 55/274 BN |
| 4,301,114 | A | 11/1981 | Rounbehler et al. | 422/52 |
| 4,312,764 | A | 1/1982 | Parshall | 210/790 |
| 4,333,735 | A | 6/1982 | Hardy et al. | 23/232 R |
| 4,333,752 | A | 6/1982 | Thies et al. | 55/387 |
| 4,335,073 | A | 6/1982 | Sherwood et al. | 422/83 |
| 4,374,786 | A | 2/1983 | McClain | 261/113 |
| 4,381,408 | A | 4/1983 | Roubehler et al. | 564/112 |
| 4,432,939 | A | 2/1984 | Watanabe et al. | 436/113 |
| 4,452,766 | A | 6/1984 | Pike | 423/242 |
| 4,460,517 | A | 7/1984 | Calaceto | 261/23 R |
| 4,473,282 | A | 9/1984 | Michlin | 354/300 |
| 4,526,755 | A | 7/1985 | Vincent et al. | 422/90 |
| 4,530,272 | A | 7/1985 | Stokes | 96/34.5 |
| 4,696,680 | A | 9/1987 | Ghate et al. | 55/25 |
| 4,701,306 | A | 10/1987 | Lawrence et al. | 422/101 |
| 4,714,482 | A | 12/1987 | Polak et al. | 55/158 |
| 4,726,824 | A | 2/1988 | Staten | 55/274 |
| 4,737,173 | A | 4/1988 | Kudirka et al. | 55/276 |
| 4,775,633 | A | 10/1988 | Rounbehler et al. | 436/106 |
| 4,847,594 | A | 7/1989 | Stetter | 340/540 |
| 4,873,970 | A | 10/1989 | Freidank et al. | 128/202.22 |
| 4,882,036 | A * | 11/1989 | Eidt, Jr. et al. | |
| 4,890,136 | A | 12/1989 | Greene et al. | 355/27 |
| 4,921,651 | A | 5/1990 | Polak et al. | 264/41 |
| 4,946,480 | A | 8/1990 | Hanville | 55/270 |
| 4,960,568 | A | 10/1990 | Matsumoto et al. | 422/83 |
| 5,001,274 | A * | 3/1991 | Bunning | |
| 5,009,678 | A | 4/1991 | Bikson et al. | 55/16 |
| 5,014,009 | A | 5/1991 | Arimoto et al. | 324/468 |
| 5,027,642 | A | 7/1991 | Wen et al. | 73/23.2 |
| 5,053,064 | A | 10/1991 | Hama et al. | 55/270 |
| 5,057,436 | A | 10/1991 | Ball | 436/113 |
| 5,061,296 | A | 10/1991 | Sengpiel et al. | 55/4 |
| 5,141,538 | A * | 8/1992 | Derington et al. | |
| 5,149,500 | A | 9/1992 | Brahmbhatt et al. | 422/31 |
| 5,185,268 | A | 2/1993 | Bonometti et al. | 436/114 |
| 5,199,263 | A * | 4/1993 | Green et al. | |
| 5,208,162 | A | 5/1993 | Osborne et al. | 436/6 |
| 5,246,668 | A | 9/1993 | MacCallum et al. | 436/116 |
| 5,262,547 | A * | 11/1993 | Ramachandran et al. | |
| 5,283,199 | A | 2/1994 | Bacon, Jr. et al. | 436/173 |
| 5,288,306 | A | 2/1994 | Aibe et al. | 95/141 |
| 5,322,797 | A | 6/1994 | Mallow et al. | 436/106 |
| 5,325,705 | A | 7/1994 | Tom | 73/31.03 |
| 5,356,594 | A | 10/1994 | Neel et al. | 422/54 |
| 5,418,170 | A | 5/1995 | Rounbehler et al. | 436/111 |
| 5,427,610 | A | 6/1995 | Croker | 95/114 |
| 5,434,644 | A | 7/1995 | Kitano et al. | 355/30 |
| 5,457,316 | A | 10/1995 | Cohen et al. | 250/286 |
| 5,563,330 | A | 10/1996 | Kimmig | 73/23.21 |
| 5,567,623 | A | 10/1996 | Rounbehler et al. | 436/158 |
| 5,582,865 | A | 12/1996 | Rezuke et al. | 427/244 |
| 5,583,282 | A | 12/1996 | Tom | 73/31.03 |
| 5,620,501 | A | 4/1997 | Tamhankar et al. | 95/92 |
| 5,622,682 | A | 4/1997 | Tom | 423/230 |
| 5,730,942 | A | 3/1998 | Megerle et al. | 422/82.01 |
| 5,739,038 | A | 4/1998 | Burrows | 436/113 |
| 5,755,839 | A * | 5/1998 | Malone | |
| 5,835,974 | A | 11/1998 | Nagy | 73/1.06 |
| 5,841,022 | A * | 11/1998 | Hase | 73/23.22 |
| 5,856,198 | A | 1/1999 | Joffe et al. | 436/100 |
| 5,955,037 | A * | 9/1999 | Holst et al. | |
| 6,002,019 | A * | 12/1999 | Tamhankar et al. | |
| 6,096,267 | A | 8/2000 | Kishkovich et al. | 422/52 |
| 6,107,353 | A * | 8/2000 | Koveal et al. | |
| 6,180,821 | B1 * | 1/2001 | Jobson et al. | |
| 6,207,460 | B1 | 3/2001 | Kishkovich et al. | 422/52 |
| 6,267,931 | B1 * | 7/2001 | Nickens et al. | |
| 6,338,312 | B2 * | 1/2002 | Hayes et al. | 118/723 CB |
| 6,468,490 | B1 * | 10/2002 | Shamouilian et al. | 423/241 |
| 6,470,760 | B2 * | 10/2002 | Shinozaki et al. | 73/863.33 |
| 2001/0015133 | A1 * | 8/2001 | Sakai et al. | 95/273 |
| 2002/0173687 | A1 * | 11/2002 | Wagner | 588/15 |
| 2003/0049190 | A1 * | 3/2003 | Irie et al. | 423/210 |
| 2003/0073293 | A1 * | 4/2003 | Ferro et al. | 438/478 |
| 2003/0129811 | A1 * | 7/2003 | Raaijmakers et al. | 438/481 |

* cited by examiner

FIG._3

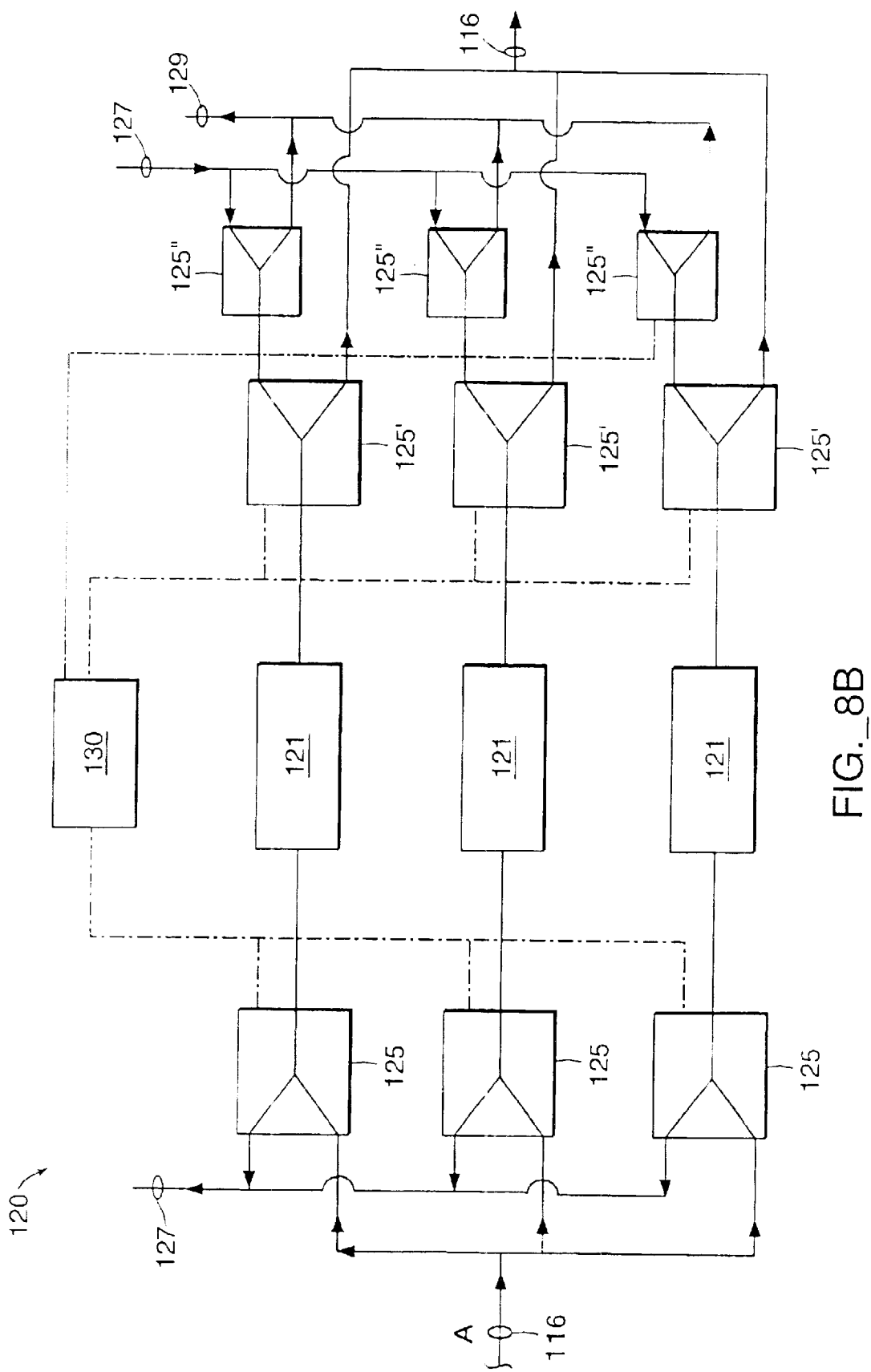
FIG._8B

DETECTION OF BASE CONTAMINANTS IN GAS SAMPLES

RELATED APPLICATION

This application is a divisional of application Ser. No. 09/232,199, filed Jan. 14, 1999, now U.S. Pat. No. 6,207,460.

The entire teachings of the above application are incorporated herein by reference.

BACKGROUND OF THE INVENTION

The invention relates to the detection of base contaminants in a gas sample, especially amine contaminants, and to systems employing such detection, including semiconductor fabrication systems and systems for filtering gases for semiconductor fabrication and other processes that require uncontaminated atmospheres of high quality.

A particular purpose of the invention is to reliably measure low concentrations of airborne base contaminants in a semiconductor manufacturing environment that may adversely affect base-sensitive photolithographic processes being employed.

In semiconductor manufacturing it has been found desirable to detect airborne basic compounds such as normal methyl pyrrolidinone (NMP) and ammonia. Such contaminants may interfere, for instance, with a photolithography process used in semiconductor fabrication. The base contaminant may react with protons produced as a result of exposure of a photoresist layer to light. This can interfere with proper exposure and development and can harm the yield of the process and the rate of production of the semiconductor wafers.

For this reason, semiconductor manufacturers have sought to measure and control the concentration of airborne molecular contamination during the critical steps of the photolithography process that are sensitive to it. A detecting instrument specific to the detection of NMP and a detecting instrument specific to the detection of ammonia have been employed in semiconductor manufacturing facilities to monitor the atmospheric quality in the vicinity of production tools.

To understand the novel aspects of the invention it is useful to mention some detection techniques that have been used in other contexts.

For study of combustion processes or atmospheric pollution, some have developed processes for measuring the total fixed gaseous nitrogen species, including $NH_3$, NO, $NO_2$, HCN and organic amines in gaseous mixtures. The process involves catalytic conversion at elevated temperature of all fixed nitrogen species to NO, followed by chemiluminescent measurement of the resulting NO concentration.

For detection of ammonia, NO and $NO_x$, machines have been made that employ an ammonia scrubber or absorber coupled with a thermal/catalytic converter with or without a molybdenum catalyst. For instance, in one instrument for stack gas analysis, a diluted sample is directed by a valve to alternatively flow through or past an absorber that specifically removes ammonia. The alternating samples proceed along a common line through a thermal converter to a chemiluminescent detector that operates in the 650–750 millibar range. By subtracting signals, the ammonia concentration can be calculated.

Another aspect of the invention relates to the use of air filters for the ambient air in semiconductor manufacturing. To avoid harm to the process from NMP or ammonia, semiconductor manufacturers have used chemical filters to remove the contaminants. These filtering systems employ filter stages within an enclosure, the filter media of each stage being penetrable by air with acceptable pressure drop. As air flows through the filtering system, unwanted contaminants are retained on the chemically active surface of the various stages of the filter system. A problem associated with such filtering systems has been to accurately predict the remaining life of the filter so that the filter media can be changed at appropriate times with minimal disruption to the use of the expensive production facility. In the case of semiconductor fabrication facilities, typically, filter life has been estimated by measuring the concentration of ammonia in the air flow associated with the filter system.

DISCLOSURE OF THE INVENTION

The measurement of ammonia, exclusive of other basic contaminants, is unsatisfactory in photolithographic processes that are affected by low concentrations of any basic contaminant gas. One process that is sensitive to low levels of any basic contaminant gas is chemically-amplified deep-ultraviolet (DUV) photoresist processing. Typically, most or all of such basic contaminants that can affect the process include nitrogen. Measurement of total fixed-nitrogen species is not applicable, however, because many of the fixed-nitrogen species (e.g., HCN, NO, $NO_2$) are not basic in nature and do not affect the process.

None of the techniques mentioned above have suggested the concept of the present invention of measuring—in a single, non-specific reading—a low-level concentration of multiple basic nitrogen compounds in a gas sample exposed to photolithographic processes and the like.

The invention is based in part on the realization that semiconductor manufacturing and certain other processes, which are recognized to be sensitive to NMP, ammonia, or other basic nitrogen compounds, are in fact sensitive to the total proton-bonding capability of all nitrogenous base contaminants present, regardless of the specific identity of the nitrogenous base contaminants. According to the invention, rather than determine the presence and concentration of each individual contaminant by a separate detector, it is realized that important advantages can be obtained by providing a detector that provides a single reading that is stoichiometrically related to the aggregate proton-bonding characteristic of various nitrogenous base contaminants that may be present in the monitored air. In this way, a "total basic-nitrogen-compound detector" is provided.

As explained further below, what is recognized to be of use is a measurement of the totality of those multiple basic-nitrogen-compound contaminants in the gas sample that can adversely affect the process being monitored. For instance, currently-employed DUV photolithography processes are sensitive to both strong and weak bases; hence, according to the present invention, all airborne basic nitrogen compounds are measured down to low concentration levels. In other cases, where the process is sensitive only to bases greater than a certain $pK_b$, then the system is implemented, according to this idea of the invention, to measure the totality of the multiple basic nitrogen compounds within the $pK_b$ range to which the process is sensitive, even at low-concentration levels.

The present invention focuses specifically on a basic-nitrogen-compound scrubber system as an important component of the entire basic-nitrogen-compound detection system. While a single ion exchange bed can be provided in a channel to remove ammonia from a gas sample flowing through the channel, this solution is not without drawbacks. Of particular concern is that ion exchange beds over time do not effectively filter basic nitrogen compounds other than ammonia. For example, NMP, a higher-molecular-weight imide, can pass through a 2-inch-deep, ½-inch-diameter scrubber in about 15 hours triggering false-negative signals in a measurement of total basic nitrogen compounds. This is a major problem which affects the functionality and reliability of the instrument's output.

In a detection system of this invention, a primary channel and a plurality of scrubbing channels are connected to a detector. The term, "detector," as used herein includes a single detection device/unit as well as a plurality of detection devices/units. Each of the scrubbing channels include a basic-nitrogen-compound scrubber. Downstream from each of the scrubbers is a converter which converts gaseous nitrogen compounds into an indicator gas and a detector for detecting the indicator gas. A primary channel also leads to the converter and detector. As used, herein, the term, "converter," refers either to a single converter unit to which all channels are connected, in parallel, or to multiple converter units individually associated with a single or multiple channels.

In a method of this invention, reference gas samples are passed through first and second scrubbers to remove basic nitrogen compounds from the gas samples. The second scrubber is purged to remove reversibly-bound nitrogen compounds while a gas sample passes through the second scrubber. The gas samples passing through either the first or second scrubber then pass through the converter and detector. Alternately, a target gas sample bypasses the scrubbers before delivery to the converter and detector. The total concentration of basic nitrogen compounds in the gas samples is then determined on the basis of the difference of the detected concentration of the indicator gas in the target gas sample and the detected indicator gas concentration in the reference gas sample.

In preferred embodiments of the system, the scrubbing channels are connected in parallel, and the system includes purge systems coupled to the scrubbers for purging reversibly-bound basic nitrogen compounds from the scrubbers. Preferably, the scrubbers include cation exchange media. A flow controller governed by a control system can be positioned to selectively control which of the scrubbing channels the sampled gas can flow through to the converter. The control system can be programmed to transfer the flow of the reference gas sample that reaches the detector from a scrubbing channel with a contaminated scrubber to a scrubbing channel with a purged scrubber and then to direct a purge gas through the contaminated scrubber. Preferably, the control system is programmed to transfer the flow of the reference gas sample away from a scrubbing channel and to purge the scrubber of that scrubbing channel before a weak-base nitrogen compound can penetrate through the scrubber. Moreover, the purging process can alternate between scrubbers with the flow of gas samples to the converter preferably continuing substantially without interruption. Finally, the control system can be programmed to alternately transfer the flow of a gas sample between the primary channel and one of the scrubbing channels.

In accordance with one aspect of the invention, the system samples gas from a photolithography tool cluster for the fabrication of semiconductor wafers and is adapted to monitor the concentration of basic nitrogen compounds in the photolithography tool cluster. In a specific form of this embodiment, the scrubbers include photoresist-coated beads, the photoresist coating matching the photoresist applied by the photolithography tool cluster.

Other preferred embodiments of the system include a pressure reducer located upstream of the detector and a vacuum pump located downstream of the detector. Further, a common converter and detection device can be coupled to the primary channel and the filtering channels. Further still, scrubbers are preferably excluded from the primary channel, and at least one multi-way valve is preferably arranged for selecting which of the channels the sampled gas may flow through to the converter.

BRIEF DESCRIPTION OF THE DRAWINGS

FIG. 8B illustrates a basic-nitrogen-compound scrubber system.

DESCRIPTION OF THE PREFERRED EMBODIMENTS

Figure 1:
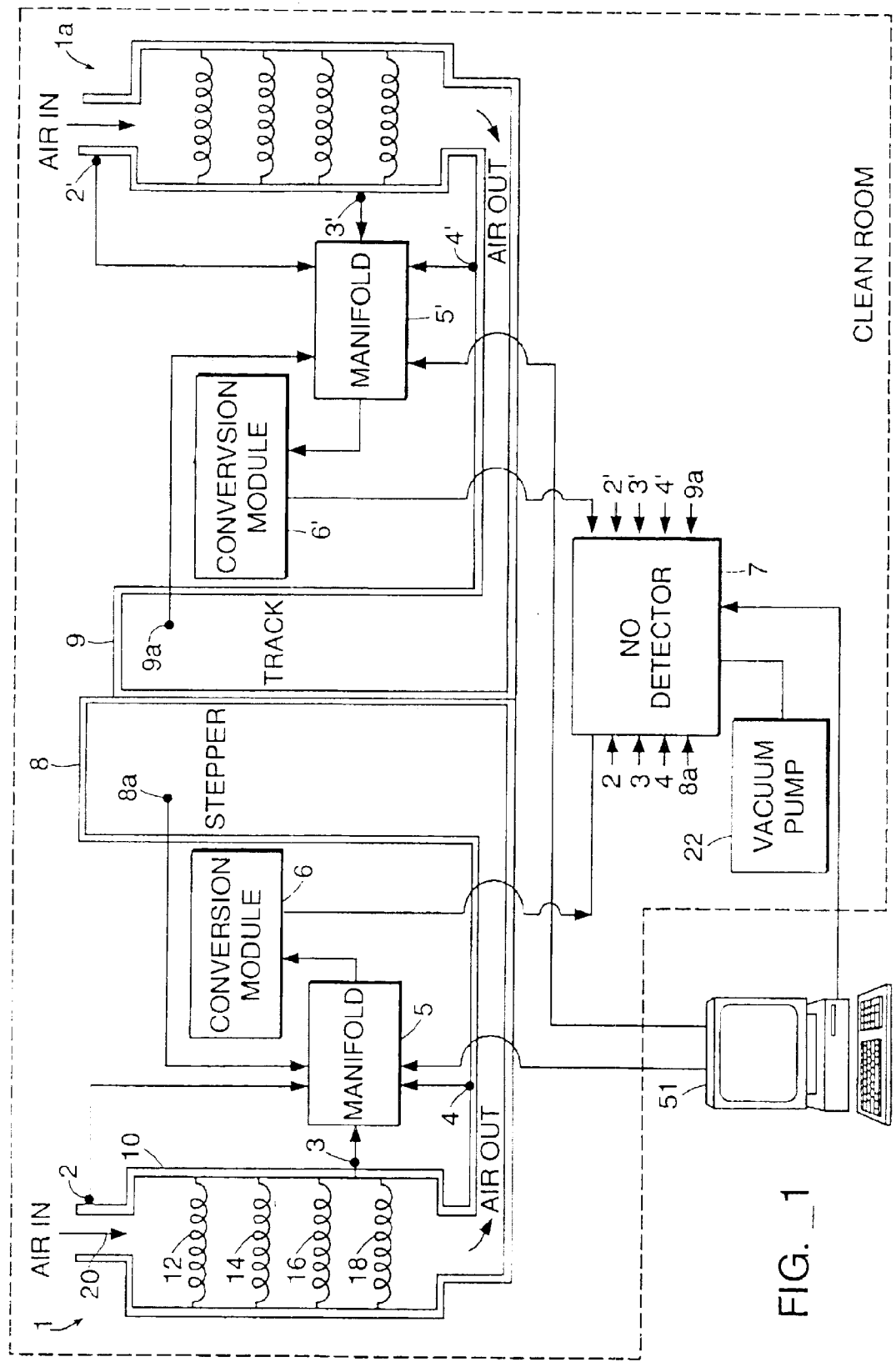
FIG. 1 is a plan view of a DUV photolithography processing facility employing a contaminant detection system.
Figure 2:
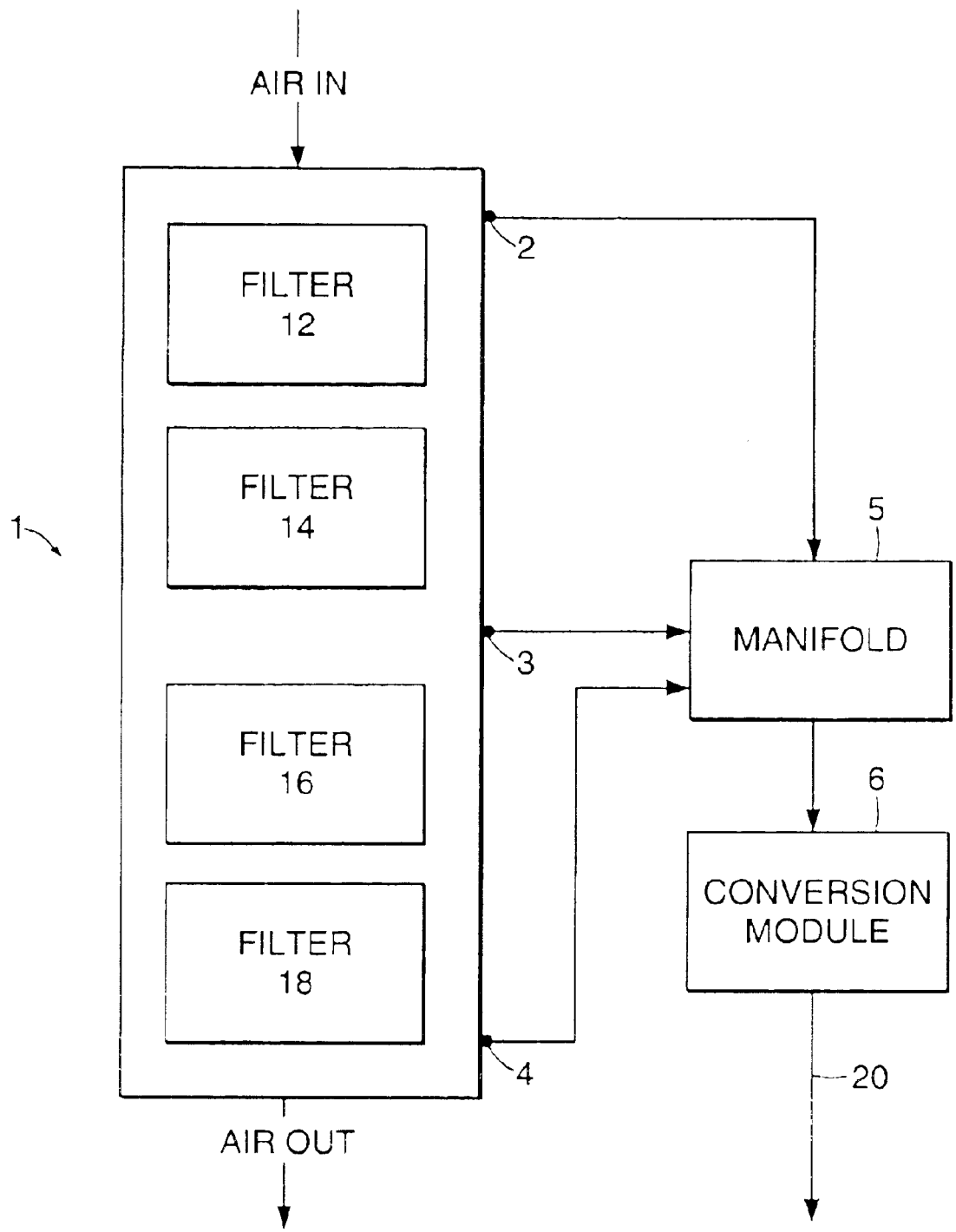
FIG. 2 is an enlarged schematic view of the filtration tower shown in FIG. 1.

In FIG. 1, a photolithography tool cluster is shown for the production of semiconductor wafers. The cluster consists of two tools, a stepper 8 and a track 9. A wafer processed by the cluster is coated with photoresist in the track 9, transferred to the stepper 8 where the coated wafer is exposed to ultraviolet radiation passing through a reticle, and then transferred back to the track 9 where the exposed photoresist is developed. Each of these tools 8, 9 is joined to a separate clean air filtration system, 1 and 1a, respectively. Each filtration tower comprises a metal enclosure 10 and a set of spaced apart chemically-active filter stages 12, 14, 16, 18 installed in series within the enclosure. As depicted in FIG.

1, the air enters at 20, at the top of the tower, the air being supplied from either outside the fabrication facility or from within the facility, or from within the clean room or the tool itself. This system and its operation are more fully described in U.S. patent applications Ser. Nos. 08/795,949, filed Feb. 28, 1997, and Ser. No. 08/996,790, filed Dec. 23, 1997, the teachings of both of which are hereby incorporated by reference.

The filters are composed of chemically-active composite materials, typically nonwoven fabric media, to which are bound activated carbon particles or ion exchange beads that have been treated to remove ammonia and organic amines. The filter media is typically arranged as a set of pleats in the enclosure. An example of such filter media is known by the trademark, Vaporsorb™, produced by the Assignee, Extraction Systems Inc. of Franklin, Mass., U.S.A.

In another embodiment, a converter-detector is employed to monitor filter performance of a filter deployed in either the make-up or recirculation air supplying a clean room. In this case, the converter-detector is employed in such a manner as to monitor total basic nitrogen compounds both upstream and downstream of a filter deployed either alone or in series in the make-up or recirculation air system of the clean room.

In other implementations, different filter media are employed. Certain examples include parallel trays of loose activated carbon particles produced by, e.g., Donaldson Company (Minneapolis, Minn., USA); extruded carbon blocks using a dry thermoplastic adhesive as the binding agent as produced by, e.g., Flanders Filters (Washington, N.C., USA), KX Industries, and Peneer Industries; thin extruded carbon blocks manifest as a fabric as manufacturing by, e.g., KX Industries; media made by the modification of the chemical properties of the fiber structure as produced by, e.g., Ebara Corp. (Tokyo, Japan) and Takuma Ltd.; and carbon fiber structures as produced by, e.g., Kondoh Ltd.; and carbon particle sheet media produced by, e.g., Hoechst-Celanese.

As shown in FIG. 1, each filtration tower, 1 and 1a, includes, respectively, an upstream sampling port 2, 2', a downstream sampling port 4, 4', and an intermediate sampling port 3, 3'. Sampling ports 8a and 9a are likewise provided for the stepper 8 and track 9, respectively. For each filter and tool combination, there is one conversion module 6 (for the stepper 8) and 6' (for the track 9). The conversion modules 6 and 6' are connected to a common, remotely-located NO detector 7.

In other embodiments, a single conversion module receives gas samples from both tools 8 and 9 and delivers the converted samples to the detector 7. In this case, the conversion module and the detector 7 can be in the form of a Model 17 instrument, which is available from Thermo Environmental Instruments Inc. (Franklin, Mass., USA). Although the remaining description relating to FIG. 1 is generally directed to the illustrated embodiment, which includes a pair of conversion modules 6 and 6', a single conversion module can generally be used with equal success.

Figure 8D:
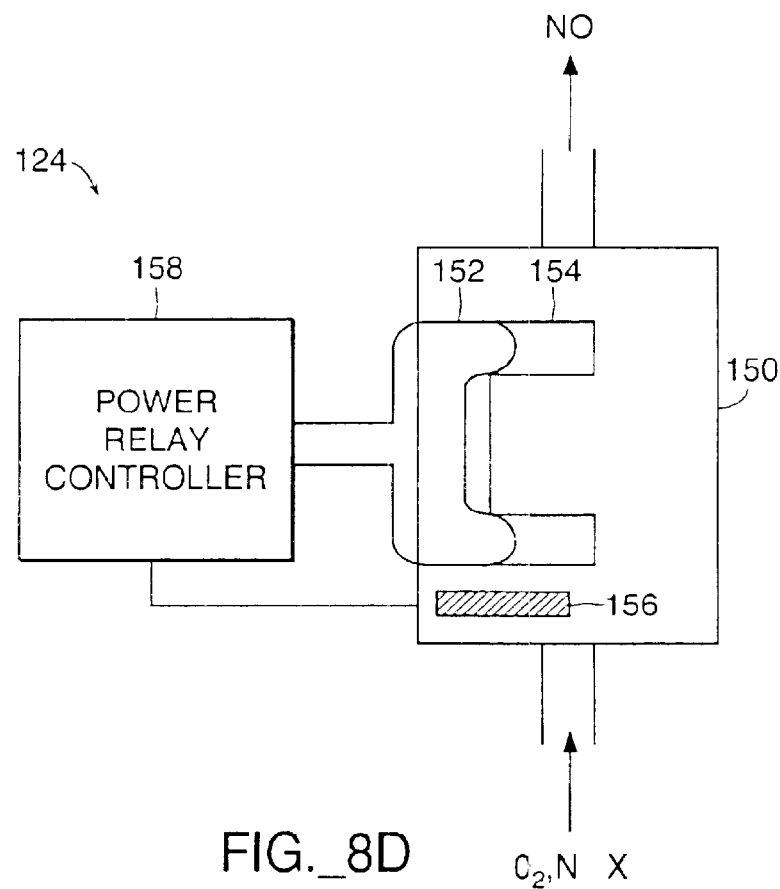
FIG. 8D illustrates a thermal converter useful in the system of FIG. 8A.
Figure 8A:
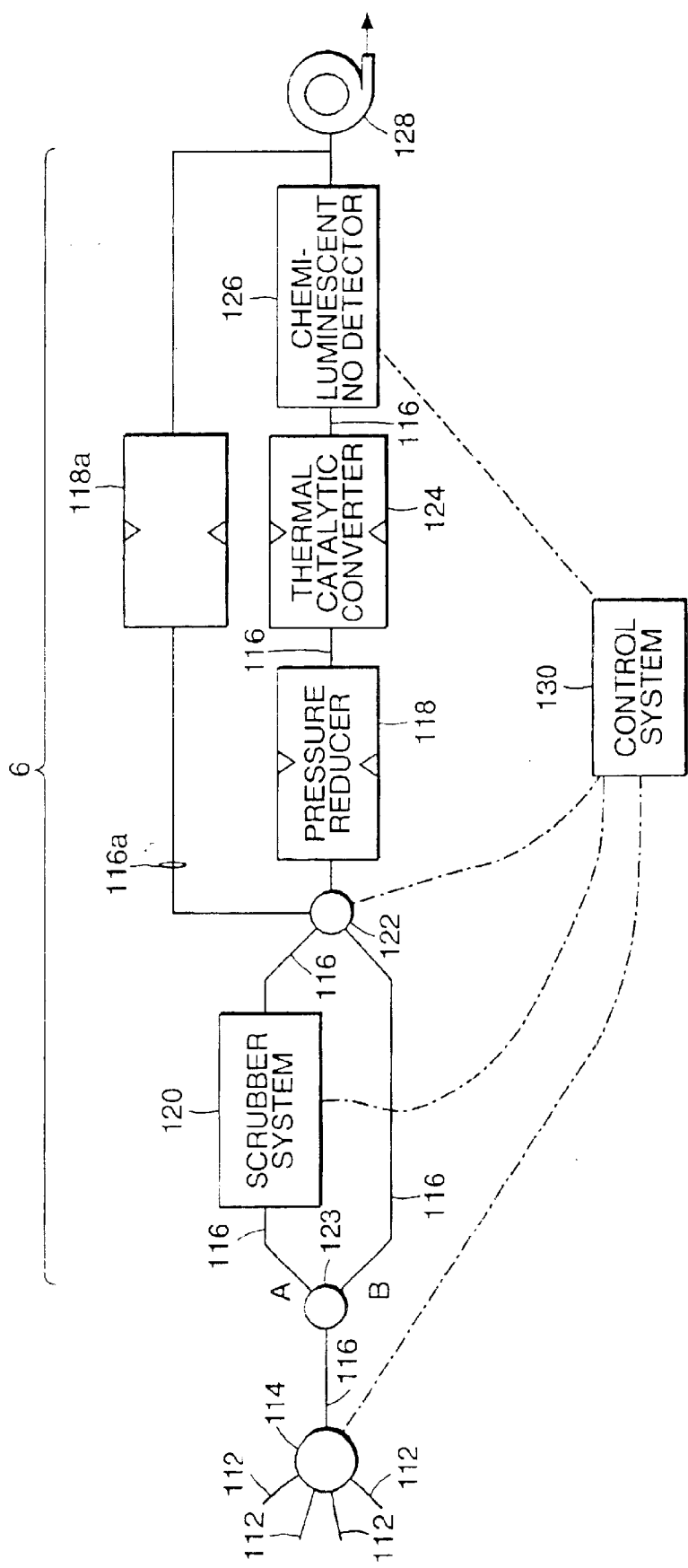
FIG. 8A is a schematic view of a sample delivery train for total basic-nitrogen-compound detection that has a scrubber system to produce an internal reference, and in which a pressure reducer is located downstream from the scrubber system.

A remotely-controlled manifold 5, 5', is associated with each conversion module 6, 6', respectively. Via respective sample lines, the manifolds 5, 5' direct to the conversion modules 6, 6' respective samples from the tools 8, 9, from the inlet streams 2, 2' of the filters, from the outlet streams 4, 4' of the filters, and from the intermediate filter ports 3, 3', according to a sequence controlled by a computer 51. As shown in FIG. 8A, and as described in greater detail, below, the conversion modules 6, 6' include a pair of channels, A and B, through which the flow of sampled gas is alternated every 10 seconds, a scrubber system 120 in channel A, a multi-way valve 122 for controlling and redirecting flow through channels A and B, a pressure reducer 118, and a thermal catalytic converter 124 in which nitrogen compounds in a gas sample are converted to nitric oxide (NO).

The converted samples are drawn from the conversion modules 6, 6' to a detector 7 by a vacuum pump 22 located downstream of the detector 7. The detector 7 includes a reaction chamber where NO is oxidized to produce electronically-excited $NO_2$ molecules and a photomultiplier tube which measures photons emitted by the electronically-excited $NO_2$ molecules as they return to their ground state.

In one embodiment, an impinger is employed to identify possible contaminants in the unconverted gas sample. The impinger consists of a glass or quartz tube holding a liquid. In this embodiment, a vacuum pump and an associated calibrated flow controller are employed to draw the gas sample from one of the sample lines through the liquid to take a grab sample. The grab sample is then analyzed or subjected to real-time colorimetric analysis, providing a quantitative assessment of the contaminating basic nitrogen compounds in the sampled gas.

In an instrument associated with more than one conversion module, each converter-detector subsystem is considered as a single instrument, which is calibrated independently of the other converter-detector subsystems. In the preferred embodiment illustrated in FIG. 1, there are two converter-detector subsystems: one subsystem serves the track 9 and its air filter system 1 and the other subsystem serves the stepper 8 and its air filter system 1a. For calibration purposes, zero air is provided by filter system 1 for the stepper subsystem and by filter system 1a for the track subsystem. By having the conversion module 6, 6' near the sampling area, the length of the sampling lines exposed to basic nitrogen compounds is reduced, which increases the response time of the system.

Figure 3:
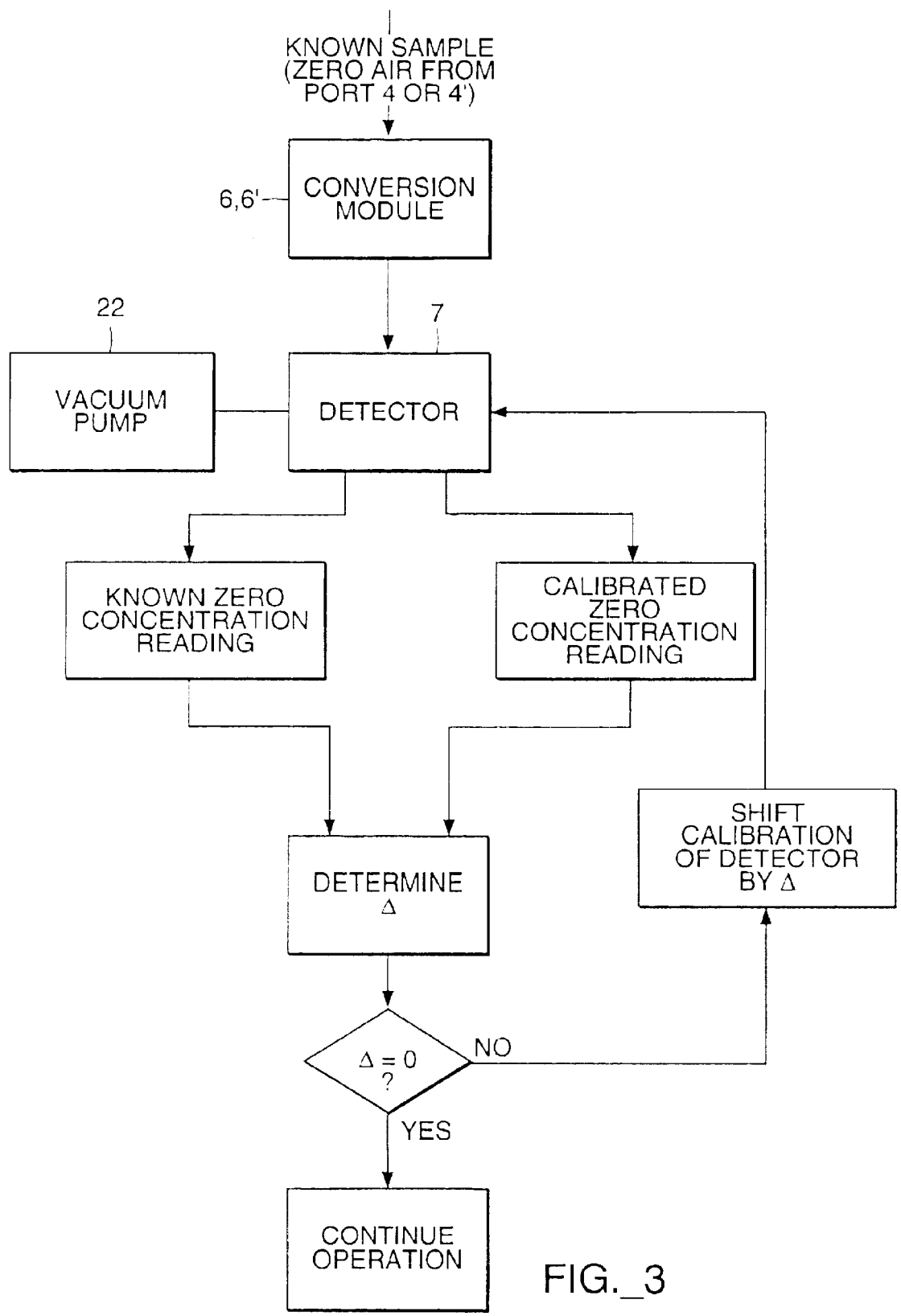
FIG. 3 is a flow diagram illustrating the process of calibrating the detection system of FIG. 1.
Figure 4:
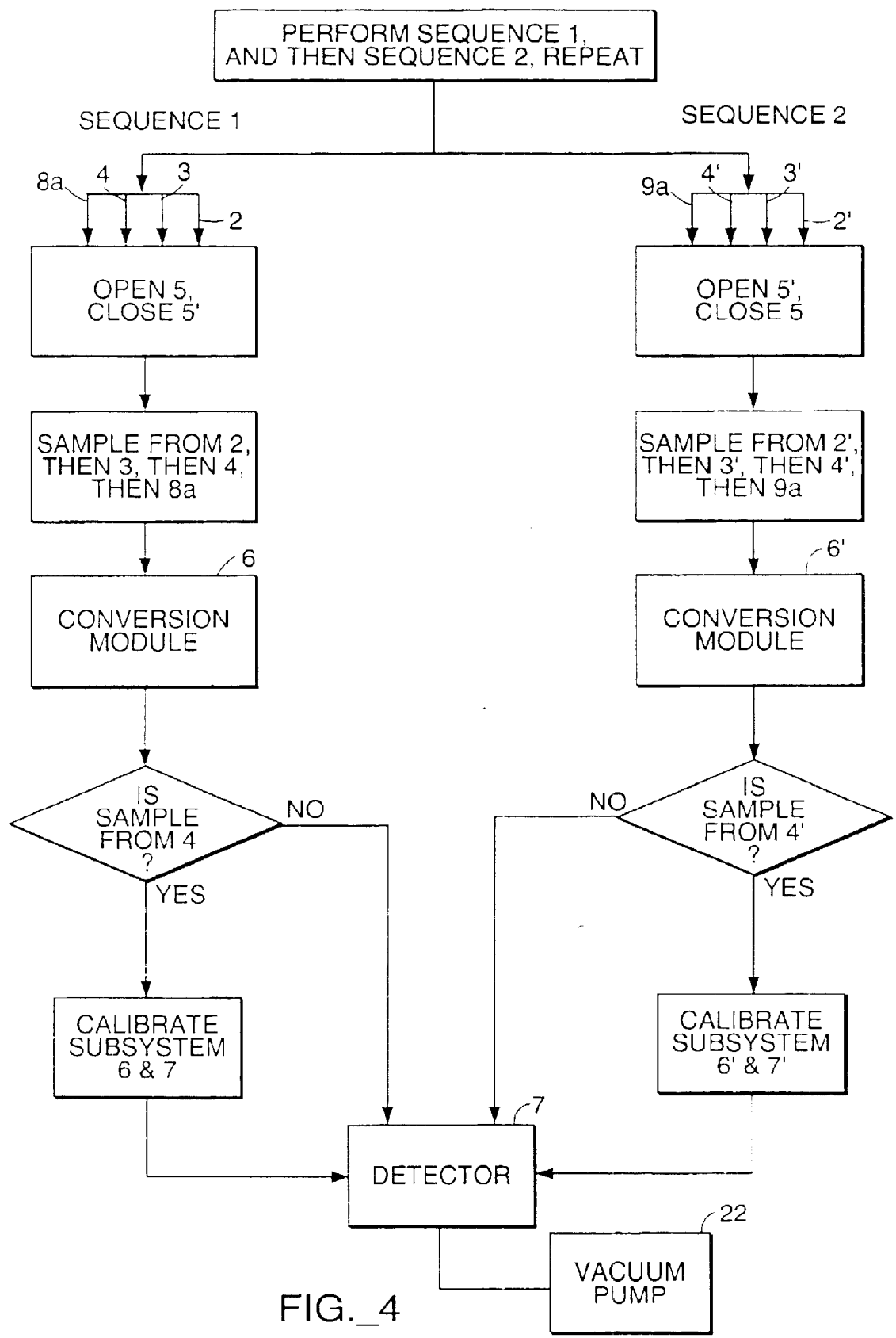
FIG. 4 is a flow diagram illustrating the continuous operation and calibration of the embodiment of FIG. 1.

To calibrate each converter-detector subsystem, two or more samples of known concentration of contaminants are provided to the instrument, as illustrated in FIG. 3. The instrument response is then compared with the known concentrations, and a calibration curve is generated and either manually or electronically, through the software, associated with the instrument to provide corrections to the instrument's response. In general, the instrument response over the concentration range remains stable for an extended period. The instrument is sensitive, however, to loss of calibration, for reasons such as drift of the photomultiplier, and the curve must be shifted relative to the true zero reading as it varies over time. Because in photolithography processing harmful contaminant concentrations are extremely low (on the order of 1 part per billion (ppb) or lower), in preferred systems the zero calibration is typically performed on the order of once a month to assure the fidelity of the zero reading. In a particularly preferred implementation, the detection system is arranged to operate continuously, as shown in FIG. 4, whereby the system performs a total basic-nitrogen-compound detection for each of the sampling ports in turn and conducts two calibrations each cycle, one with respect to each of the conversion modules 6, 6' with which the detector 7 operates.

Preferably, the zero air employed for calibration is provided by the outlet ports 4 and 4' of the filtration system (see FIG. 1). The instrument is then instructed to provide a zero reading for the calibration sample. In the case that the difference between the total basic-nitrogen-compound reading for the outlet port 4 and the sample at the intermediate port 3 is not greater than zero, the sample from the outlet port 4 is employed to establish zero air. In another preferred embodiment, a sampling port located just preceding the last filter stage is employed to verify that the zero air from the output of the filter stack is in fact zero air. Also, in an alternative embodiment, a builtin, dedicated, zero air generator is employed. The generator provides zero air by either filtering the ambient air or by bubbling air through a liquid scrubber solution.

An external computer, preferably situated outside the clean room in which the tools are located, is employed to control the operation and monitor the entire photolithography process. The software is customized for the required application. Performance data is provided to the computer to provide an archival database to be employed to give the contamination history of the tool cluster.

Based on the particular ports being sampled, the software employed in the operation of the instrument determines which converter-detector subsystem is to be calibrated and the appropriate source of zero air for calibration purposes. The software also designates which calibration curve to employ. As the detection system is calibrated and the new zero readings are determined, the calibration curves are adjusted accordingly.

Figure 5:
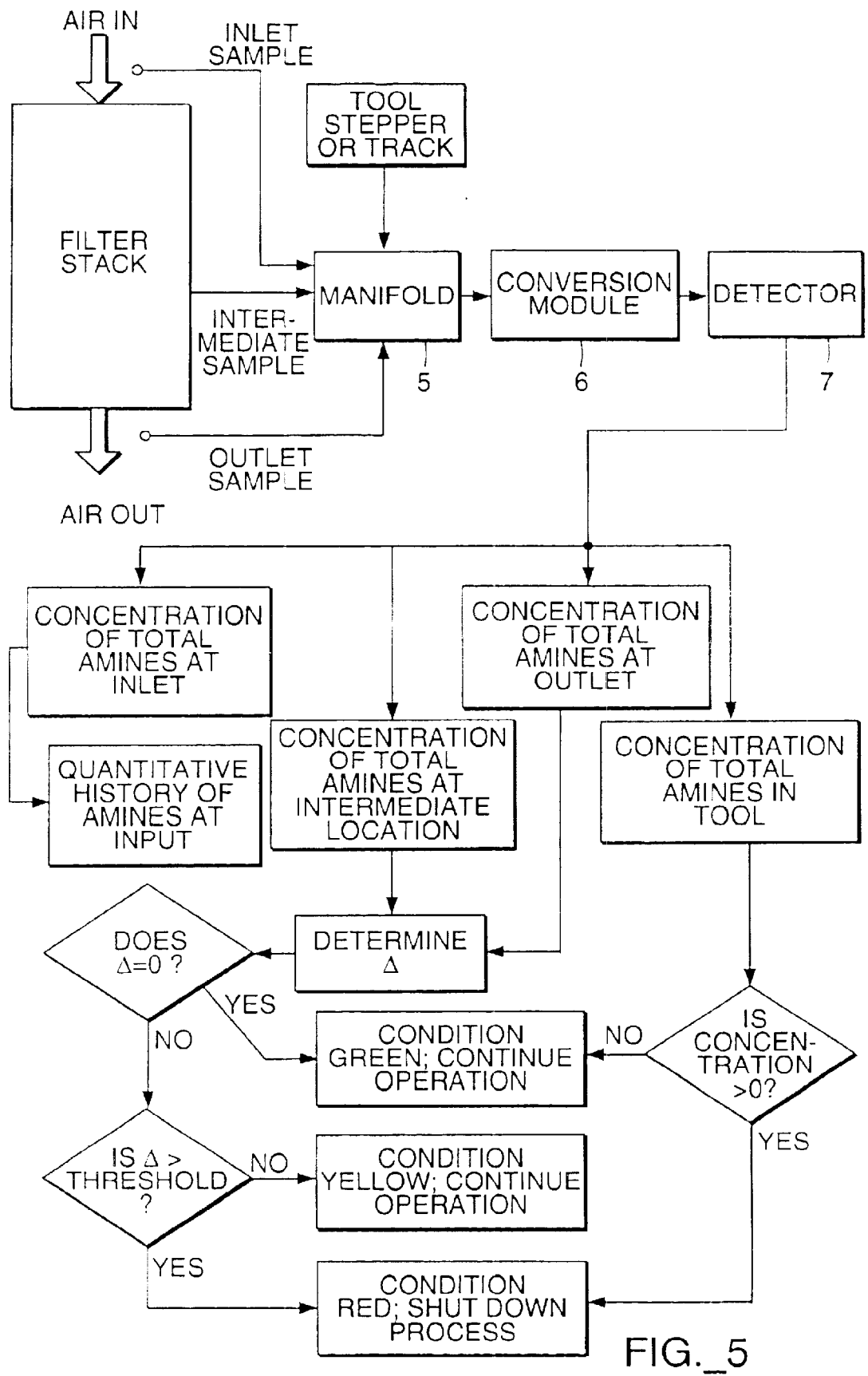
FIG. 5 is a flow diagram illustrating the monitoring and control of the processing tools and filtration system of the embodiment of FIG. 1.

In a desired application, control instrumentation, as illustrated in FIG. 5, monitors the performance of the filtering system and the level of contamination at the track and stepper tools. Should a reading from either the stepper or track exceed a predetermined threshold, an alarm is enabled and the process is immediately shut down. However, by use of this detection system, the occurrence of such an emergency can normally be avoided.

As shown in FIG. 5, the filtering system is continuously monitored in real time, as follows. The sample at the inlet to the filter system, over time, provides a quantitative history of the input of basic-nitrogen-compound contaminants to the filter. By using samples drawn from the intermediate position along the filter system as well as from the outlet of the filter stack, and by measuring the difference in concentration levels from these locations, one of the following steps is triggered. If the difference is zero (condition green) and the total amine or Bronstead base concentration at the tool is within operating limits, then the operation continues without interruption. When the difference is greater than zero, the difference is compared with a predetermined threshold. If the threshold is not exceeded (condition yellow), operation continues but a filter replacement is scheduled. If the threshold is exceeded, or if the total basic nitrogen compound detected at the tool exceeds operating limits (condition red), the operation is immediately shut down.

In another embodiment, there are three or more conversion modules remotely located at various locations in the fabrication facility. One conversion module is employed to monitor the general conditions in the clean room; a pair of conversion modules is employed to monitor the contamination around a different tool cluster; another conversion module is employed to monitor the contamination level within a chemical storage cabinet to provide early indication of chemical spills.

Figure 6:
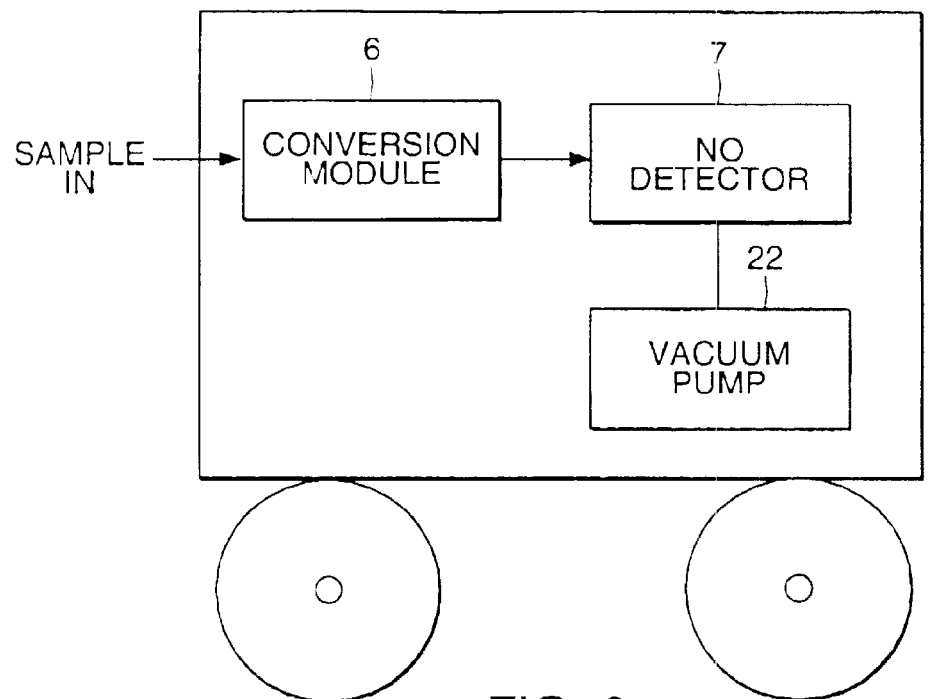
FIG. 6 is a schematic view of a total basic-nitrogen-compound detector as a mobile detection unit.

In another implementation, shown in FIG. 6, the converter-detector instrument is constructed as a mobile leak detector. The mobile unit is moved to selected regions of the fabrication facility to seek possible areas of contamination leaks. By following an escalating basic-nitrogen-compound concentration trend, the mobile unit localizes the source of the contamination.

Figure 7:
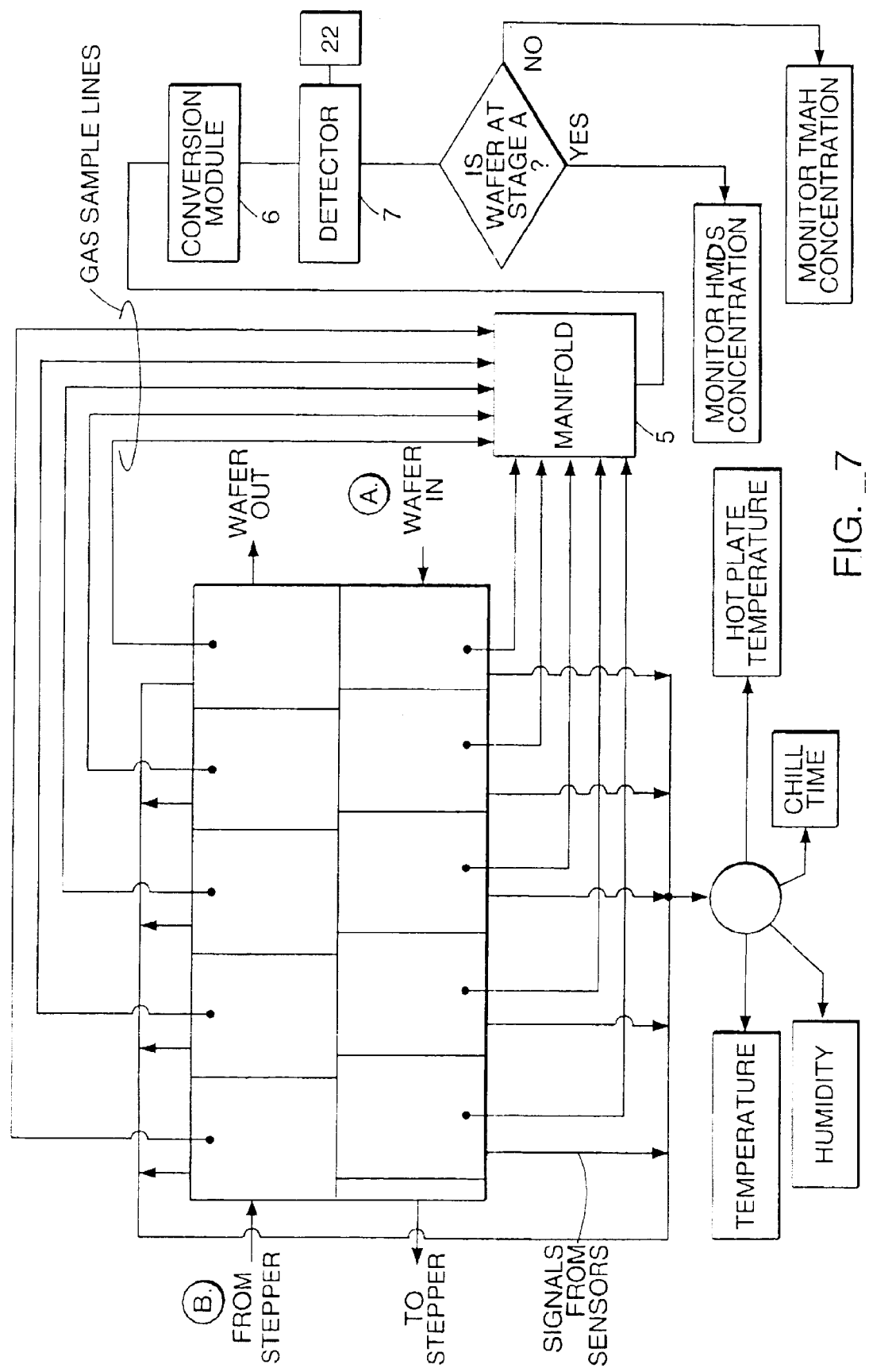
FIG. 7 is a schematic view of a photolithographic system in which a total basic-nitrogen-compound detector is combined with a track.

In another embodiment, illustrated in FIG. 7, the system is combined with a multi-point sampling system of an array of sensors to monitor the operating status of a track, including temperature, temperature of the hot plate, time on the chill plate, exposure time, etc. A total basic-nitrogen-compound detector monitors process contaminants, such as the concentration of an adhesion promoter, e.g., hexamethyldisilozane (HMDS), in a gas sample during the coating stage when photoresist is applied to the semiconductor wafers. The wafers are then sent to the stepper for exposure and subsequently brought back to the track for developing. During this stage, another, or the same, total basic-nitrogen-compound detector monitors the concentration of another possible internally-processed chemical contaminant, such as tetremethylammonium hydroxide (TMAH), employed in the developing stage.

The system enables, in its total basic-nitrogen-compound reading, the simultaneous detection of NMP and ammonia, which previously were typically monitored with separate detectors. The system also enables detection, in its total basic-nitrogen-compound reading of other basic nitrogen compounds that are known to be harmful to the photolithography process, such as morpholine, diethylamine ethanol, and cyclohexylamine, agents which are commonly used to inhibit corrosion in high-humidity regions. Basic nitrogen compounds from the facility cafeteria, especially seafood, are also included in the detection as well as basic nitrogen compounds from the breath of the facility workers, which can create high levels of basic-nitrogen-compound contamination, depending upon diet and smoking habits. As has been explained, the system, as illustrated, converts substantially all such airborne basic nitrogen compounds to a common detectable compound, which it detects to indicate the level of hydrogen-bonding contaminants. If high concentrations of the contaminants are detected, by grab sampling techniques, the exact sources of the contamination can be determined and remedied.

Another advantageous aspect of the system is its adaption to the certification process of clean rooms. Heretofore, during the certification process, each individual molecular base present in the clean room was typically detected by a separate detector. The concentrations were summed providing a number indicating the total base loading in the clean room. For instance, if three bases were present, each with a concentration of 10,000 parts per trillion (ppt), the clean room rating would be MB30,000 (or 30,000 ppt). the present invention solves the problem of detecting individual bases by providing the total base loading within a clean room with a single reading.

The following embodiments of the invention are particularly effective in providing an accurate determination of total basic nitrogen compounds at low concentrations, for protection of the base-sensitive processes. These embodiments include a primary channel and a plurality of scrubbing channels for delivering gas samples from a source to the converter and detector. Each of the scrubbing channels includes a removal device for removing basic nitrogen compounds from the gas samples to produce reference samples. In some embodiments, the removal device is process-specific, meaning that it removes only those basic compounds that are of interest for a specific process. For example, in an embodiment specifically designed for use with semiconductor fabrication tools, the removal device is coated with photoresist to remove from the gas sample those compounds that will interfere with photolithographic deposition and development. The primary channel, meanwhile, delivers target gas samples from the same source to the convertor without scrubbing.

Because the scrubbing channels produce a reference sample that is free of substantially all of the gas molecules corresponding to the class of basic nitrogen compounds of interest, the reference sample provides a baseline for canceling the effects of background, nitrogen-containing contaminants which might otherwise contribute to the NO concentration detected by the chemiluminescent detector in the target gas sample.

Referring to FIG. 8A, a sample delivery train, including a conversion module 6, is shown for determining the total basic-nitrogen-compound concentration in a gas sample using an internal reference for zero air (i.e., air that is free of basic nitrogen compounds). The sample enters through a selection valve 114 (e.g., a multi-position valve manufactured by Vici Co., Houston, Tex., USA), which creates an open flow path from one of the sampling ports 112. From the selection valve 114, the sample is directed to the conversion module 6, which splits each incoming sample into two parts, channels A and B, and directs each part separately, via a multi-way valve 122, to a thermal catalytic converter 124 followed by a chemiluminescent detector 126. Alternatively, a pair of three-way valves (illustrated as valves 122a and 122b in FIG. 8C and connected as shown) can, in practice, be substituted for the multi-way valve 122. Another valve 123 is provided upstream from the scrubber system 120 to help direct the flow of the gas sample into channels A and B and to prevent backflow through the channels.

Channel A, which serves as a "scrubbing channel," directs part of the sample through a basic-nitrogen-compound scrubber system 120 and then to the valve 122, while channel B, referred to as the "primary channel," directs part of the sample directly to valve 122. The term, "scrubber," as used in this document is intended to refer to any device that is effective for removing basic nitrogen compounds, or a device that otherwise treats the basic nitrogen compounds in such a way that they have no effect on the response of the detection system being employed.

The scrubbed and unscrubbed parts of the original sample from channel A and B, respectively, proceed from valve 122 through the thermal catalytic converter 124 to the chemiluminescent detector 126 as time-separated samples in a single conduit. The difference between the response of the chemiluminescent detector 126 to samples from channel A and B reflects the total basic-nitrogen-compound concentration in the original sample of gas.

It has been determined that the sensitivity of basic-nitrogen-compound detection improves as the operating pressure of the chemiluminescent NO concentration measurement decreases. Accordingly, the chemiluminescent NO detector 126 operates at a pressure of 125 millibar or less, by co-action of vacuum pump 128 and an upstream pressure reducer 118, to achieve a low noise level and to achieve a detection sensitivity of 1 part per billion (ppb), preferably 0.5 ppb, or better. Though the ideal operating pressure in the detector 126 is a function of the gas flow rate through the detector in any given application, a preferred pressure level in the detector is generally about 40 mbar (about 30 Torr).

The conversion module 6 initially takes a sample of gas from one of the sampling ports 112 via selection valve 114 and channels it through one of the sample lines 116. Sample lines 116 are tubes formed of Teflon® PFA from E. I. DuPont de Nemours of Wilmington, Del., USA. Alternatively, sample lines 116 can be stainless steel tubes coated with CVD-coated silica (e.g., Silcosteel™ from Restek Corp., Bellefonte, Pa., USA). Sample lines coated with silica are nonporous and nonreactive and, therefore, have little effect on ammonia and organic amines passing through the tubes. In contrast, commonly-used tubing of PTFE is relatively porous and tends to emit hydrogen fluoride, a strong acid, which reacts with ammonia and amines, interfering with the measurement of total basic nitrogen compounds. Silica may be deposited onto the stainless steel tubing using chemical vapor deposition. In certain applications, sample lines comprising glass are used. The glass sampling lines may be reinforced with epoxy.

In certain advantageous embodiments, sample lines 116 are heated substantially along their total length to approximately 50° C. using electrical heating lines (see, e.g., U.S. Pat. No. 3,727,029, incorporated herein by reference). This reduces the tendency for basic nitrogen compounds to deposit on the walls of the tubing (reduces basic-nitrogen-compound-sticking coefficient) and thus reduces sample line contamination of the alternating sample gas slugs.

In this context, the combination of heating the sample lines along with using a silica coating on the lines is advantageous because it reduces both contamination of the gas sample and deposition of gas sample components. Nevertheless, the practice of heating sample lines of other compositions, by itself, can provide a beneficial effect. Heating is preferably accomplished using electrical resistance wire incorporated in the wall of the sample line or otherwise disposed in thermal contact with it.

Selection valve 114 (e.g., a multi-position valve manufactured by Vici) enables samples from different locations to be channeled into a single conversion module 6. The gas sample then flows through channel A or B to multi-way valve 122. After exiting valve 122, the gas sample passes through a pressure reducer 118 (e.g., a flow restrictor, such as a capillary glass tube or a small orifice), where the pressure drops from atmospheric pressure on the upstream side of pressure reducer 118 to approximately one-tenth atmospheric pressure on the downstream side. This pressure drop is maintained by vacuum pump 128 positioned downstream of detector 126. The pressure reducer 118 is preferably positioned downstream of the scrubber system 120 because the scrubber system 120 operates with greater effectiveness at higher pressures. Preferably, the pressure reducer 118 comprises a calibrated glass capillary heated to 50° C. to reduce the basic-nitrogen-compound sticking coefficient. The pressure reducer 118 can be made from tubes of glass, ceramic, stainless steel, quartz, or stainless steel with an interior plated with gold or other inert material. The low pressure of the samples-created by pressure reducer 118 and vacuum pump 128, in addition to enabling high sensitivity detection, reduces the response time for measuring total basic-nitrogen-compound concentration. This is because the samples travel through the delivery train rapidly; for instance, in the system described, valve 122 may be shifted between channels A and B every 10 seconds in normal operation.

Auxiliary conduit 116a is connected at one end to valve 122, At its opposite end, auxiliary conduit 116a is connected to the vacuum pump 128. Auxilary conduit 116a includes a pressure reducer 118a to limit flow therethrough. During operation, valve 122 connects the non-selected channel A or B to the auxiliary conduit 116a to maintain a gas flow through the non-selected channel. In this way substantially-steady-state flow conditions can be maintained in the scrubber system 120, and fresh sample is immediately available to the converter 124 upon actuation of valve 122. Further, the steady-state flow of gas through the channels reduces the incidence and magnitude of pressure spikes that can occur upon switching and thereby produce erratic instrument readings.

The components of a scrubber system 120 of this invention are illustrated in FIG. 8B. The scrubber system 120 includes three scrubbers 121 connected in parallel to the sample line 116. The scrubbers 121 of channel A are constructed to selectively remove from the gas sample the totality of the basic nitrogen compounds to which a photolithographic or other process being guarded is sensitive, yet their construction and function are nevertheless such as to not affect other nitrogen-containing compounds. Each scrubber 121 is preferably a solid-state scrubber, comprising an ion exchange medium with active sulfonic or carboxylic groups. The ion exchange medium is substantially non-hygroscopic and nonporous. The medium can be in the form, for example, of either fibers or a resin. The scrubber may also comprise any material that preferentially binds the airborne molecular bases (e.g., photoresist-coated substrates, weak acid-coated substrates, strong acid-coated substrates, ion exchange materials, or chemically-treated activated carbon and molecular sieves). The properties of the active media can be chosen to optimize the selectivity of the detection process. Further still, the scrubber can be a chemical gas filter medium, along the lines of the air filter that supplies "zero air" in the previously described embodiments.

A strong cation exchange medium is preferred as the scrubber substance in the scrubbers 121 of FIG. 8B. The medium within basic-nitrogen-compound scrubber 121, being a strong acid, removes multiple molecular bases, such as ammonia and other basic nitrogen compounds. A strong cation exchange medium ensures removal of both strong and weak molecular bases, and is suitable for photoresist lithography techniques that are sensitive to both strong and weak bases. For techniques sensitive only to strong bases, a weaker acid ion exchange medium may be employed, so that weak bases are not removed and occur equally in the scrubbed and unscrubbed samples.

Nevertheless, even when a strong cation exchange medium is used, chromatic differences in removal efficiency will develop over time. A strong base, such as ammonia ($NH_3$), will be tightly bound to the cation exchange medium and, once it is removed from the gas sample, will likely remain fixed to the scrubber. A weak base (typically, one with a high molecular weight, such as NMP), however, will tend to gradually drift through the scrubber, repeatedly binding to and releasing from the cation exchange medium. Gradually, over a matter of hours, NMP will work its way through and out of the scrubber. When a tube that is ½ inch in diameter and 2 feet in length is used with a flow rate of 1 liter per hour, NMP will pass through the scrubber in about 15 hours. Bases with strengths between that of ammonia and NMP will gradually drift through the scrubber, albeit at rates slower than that of NMP.

Nine three-way valves 125, 125' and 125" act as flow controllers, controlling the flow of sampled gas and purge gas through the scrubbers 121. The valves 125, 125', 125" in turn, are controlled by a control system 130. When a pair of valves 125, 125' on opposite sides of the same scrubber 121 both open channels to the sample line 116, sampled gas flows through that scrubber 121, with the scrubber 121 filtering basic nitrogen compounds from the sampled gas.

In one embodiment, the control system 130 selectively opens the channels to the sample line 116 in a single pair of opposing valves 125, 125' at a given moment. The control system then cyclically redirects the flow from the sample line 116 to each of the scrubbers 121, in sequence. The duration of flow (which is still received as a series of pulses, alternating with channel B, shown in FIG. 8A) through each scrubber 121 is limited to less than the time required for a high-molecular-weight contaminant to pass through the scrubber 121. Preferably, the gas flow is shifted among scrubbers 121 about every 2 to 3 hours. After the flow has been redirected from a scrubber 121, the control system 130 then sends a signal to respective valves 125, 125' and 125" to open a channel from the purge line 127 through the respective scrubber 121 and out the purge line exhaust 127', illustrated on the left side of FIG. 8B. The purge line 127 is supplied by a source of compressed purge gas (typically, air from which bases have been filtered), which flows through valves 125" and 125' and then to scrubber 121, so that the purge gas flows through the scrubber 121 in a direction opposite to the prior flow of the sampled gas. The purge gas is directed through each scrubber 121 via its respective valves 125, 125' and 125" in a sequence following that of the sampled gas flow and also for a period of about 2 to 3 hours. Accordingly, the purge gas cleanses each scrubber 121 of basic nitrogen compounds removed from the sampled gas. Consequently, a clean scrubber 121 is always available when the flow of sampled gas is redirected.

In addition to being connected to valves 125' and to the purge line 127, valves 125" are also connected to an exhaust line 129. In one embodiment, the control system 130 regulates valves 125, 125' and 125" to maintain a flow of sampled gas through each of the scrubbers 121 at all times, except during purging. The flow through only one of these scrubbers 121 is directed back to the sample line 116, however. Sampled gas flowing through other, inactive scrubbers 121 is directed by the valves 125' and 125" into the exhaust line 129, which removes the sampled gas from the system. The purpose of maintaining gas flow through "inactive" scrubbers is to keep "inactive" channels conditioned so that when the gas flow is redirected to a purged scrubber 121, the detector readings are less likely to be skewed by a momentary spike due to the need to flush old gas from the newly-activated scrubber 121 after a shift.

The sample in channel A, upon exiting scrubber system 120, contains essentially no detrimental molecular bases; i.e., total concentration of objectionable basic nitrogen compounds is approximately zero. This basic-nitrogen-compound-free sample becomes the reference sample for purposes of measuring the total basic-nitrogen-compound concentration in the unscrubbed sample from channel B. The scrubbers, however, do not affect neutral or acidic nitrogen-containing compounds. Otherwise, a false signal would be produced because those same compounds remain in the target sample.

Figure 8C:
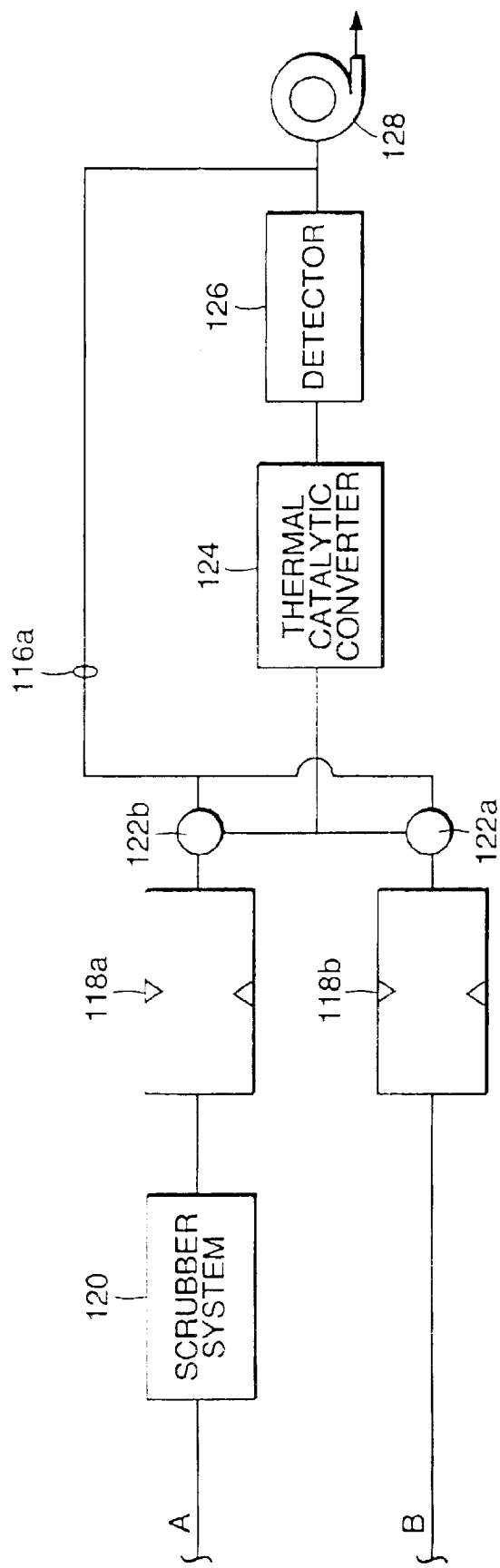
FIG. 8C illustrates a sample delivery train with separate pressure reducers.

In other embodiments, the reference gas and the target gas may be sampled from different inputs. In these embodiments, it is desirable to construct channels A and B to have the same pressure drop from the input location to the converter input. Referring to FIG. 8C, separate pressure reducers 118a, 118b may be used in channels A and B. To ensure that the pressure drop in each channel is approximately the same, pressure reducer 118a in channel A contains a larger orifice than pressure reducer 118b to compensate for the affect of basic-nitrogen-compound scrubber system 120 on the pressure in channel A. Thus, the pressure drop between scrubber system 120 and three-way valve 122a is equivalent to the pressure drop between pressure reducer 118b and three-way valve 122b.

Valves 122a and 122b allow the basic-nitrogen-compound-free sample from channel A and the unscrubbed sample from channel B to be directed to thermal catalytic converter 124 alternately, in rapid sequence. Operating the delivery train at 125 millibar pressure, for example, enables the three-way valves 122a and 122b to jointly switch the flow of sample gas between channel A and channel B several times per minute, to enable averaging of a number of readings, if desired, within a short monitoring interval, for instance ten minutes or less. While either valve 122a or valve 122b directs a gas sample from one channel through the thermal catalytic converter 124 and detector 126, the other valve 122a or 122b maintains continuous flow through the other channel by directing gas that passes therethrough into auxiliary conduit 116a.

Thermal catalytic converter 124 (e.g., as manufactured by Thermo Environmental Instruments Inc.) converts basic nitrogen compounds in each gas sample to nitric oxide (NO) by thermal oxidation. A suitable catalytic converter 124 is illustrated in FIG. 8D. The converter 124 comprises a reaction chamber 150 that may or may not contain a catalytic element 152 (e.g., platinum and/or palladium), a heating element 154 to heat the reaction chamber, and a thermocouple 156 connected to power control relay 158 which regulates the temperature of the reaction chamber. Since any given sample from channel B may contain a variety of basic nitrogen compounds (such as morpholine, diethylamino ethanol, ammonia, and normal methyl pyrrolidinone), thermal catalytic converter 124 must have a high conversion efficiency for many types of basic nitrogen compounds. To achieve a high conversion efficiency (85–100%) for a broad range of basic nitrogen compounds, a stainless steel surface heated to 900° C. is used as the catalyst. Alternatively, a metal oxide surface can be used. The gas sample is oxidized as it passes over the heated surface resulting in the conversion of basic nitrogen compounds to NO. If the gas sample lacks oxygen for oxidation, oxygen gas should be supplied to the converter.

In other embodiments, the converter may perform photocatalysis, wherein the bonds of nitrogen-containing molecules are split with ultraviolet light to free nitrogen atoms for oxidation to thereby form NO. The appropriate conversion technique is determined by the desired application, taking into account cost and conditions of use.

In some applications, gas samples entering thermal catalytic converter 124 may contain molecules that are not basic nitrogen compounds, but will nonetheless be converted into NO. For example, compounds such as $NF_3$, HCN and $CH_3CN$ are not basic nitrogen compounds, yet if present in the gas sample, will be converted to NO in thermal catalytic converter 124. These compounds will not affect the total basic-nitrogen-compound concentration calculation, however, because the basic-nitrogen-compound scrubbers 121 do not retain these compounds since they are not bases. As such, samples from channel A and channel B contain equal amounts of these non-basic compounds, and thermal catalytic converter 124 converts these compounds to NO equally for channel A and channel B, thus canceling out any effect.

Likewise, where the process to be monitored is sensitive only to strong bases, scrubbers that include a medium, e.g., a weak acid, that removes only the various strong-base nitrogen compounds are selected. In this case, since the weak-base nitrogen compounds will be present in both channels, their presence does not affect the response of the system. Alternatively, basic nitrogen compounds can be differentiated on the basis of strength by using converters that convert bases of different strengths with different efficiencies.

Converted samples exit thermal catalytic converter 124 and enter chemiluminescence detector 126 (e.g., as manufactured by Thermo Environmental Instruments, Inc.). The detector 126 employs chemiluminescence for NO detection. Typically, the maximum signal from chemiluminescence detector 126 is achieved at a pressure of about 65 Torr and at a flow rate of about 1.5 liters per minute under the operating conditions described above. Detector 126 operates at approximately 125 millibar, suitable for detection of low concentrations of basic nitrogen compounds. This high sensitivity affords detection of total basic-nitrogen-compound concentrations of less than 1 ppb, preferably less than 0.5 ppb.

Detector 126 employs chemiluminescence for NO detection. For this purpose $$NO + O_3 \rightarrow NO_2^* + O_2,$$

NO is caused to react with ozone generated by an internal ozone generator in a reaction chamber of the detector 126. This produces electronically-excited $NO_2$ molecules ($NO_2^*$), which, in returning to the ground state, emit photons, hv, that are detected by an appropriately-cooled photomultiplier tube. The reaction is given by the expression, $$NO_2^* \rightarrow NO_2 + h\nu.$$

To achieve the needed sensitivity for current DUV photolithographic processes with presently-available photomultipliers, the photomultiplier tube is cooled at least to −5° C. To achieve sensitivities required for next-generation fine-resolution DUV photolithography in semiconductor manufacturing, the tube is cooled to −15° C. by an associated thermoelectric cooler. Moreover, since there is significant variation in the sensitivity of photomultiplier tubes produced by the same manufacture, the analyzer sensitivity is further increased by testing and choosing an optimum photomultiplier tube for the performance required. In other implementations, NO is detected by colorimetric methods using devices available from, e.g., Tytronics, Inc. of Bedford, Mass.; other methods that are based upon continuous in-line sampling may also be used.

The signal from the photomultiplier is converted into time-based NO concentration values by a control system 130, and then the total basic-nitrogen-compound concentration of the gas sample from the selected sampling point is determined, e.g., by appropriately averaging and differencing the values. The total basic-nitrogen-compound concentration for the gas sample equals or is proportional to (accounting for incomplete NO conversion of basic nitrogen compounds) the difference between the NO concentration of the unscrubbed sample from channel B, e.g., at time $t_1$ (or the average of NO concentrations at times $t_1, t_3, \ldots t_{n-1}$, n being an even number) and the NO concentration for the basic-nitrogen-compound-free sample from channel A, e.g., at time $t_2$ (or the average of NO concentrations determined at times $t_2, t_4, \ldots t_n$, n being an even number).

In an alternative embodiment, the detector 126 comprises a plurality of detection devices, with a separate detection device being allocated to each channel.

Figure 8E:
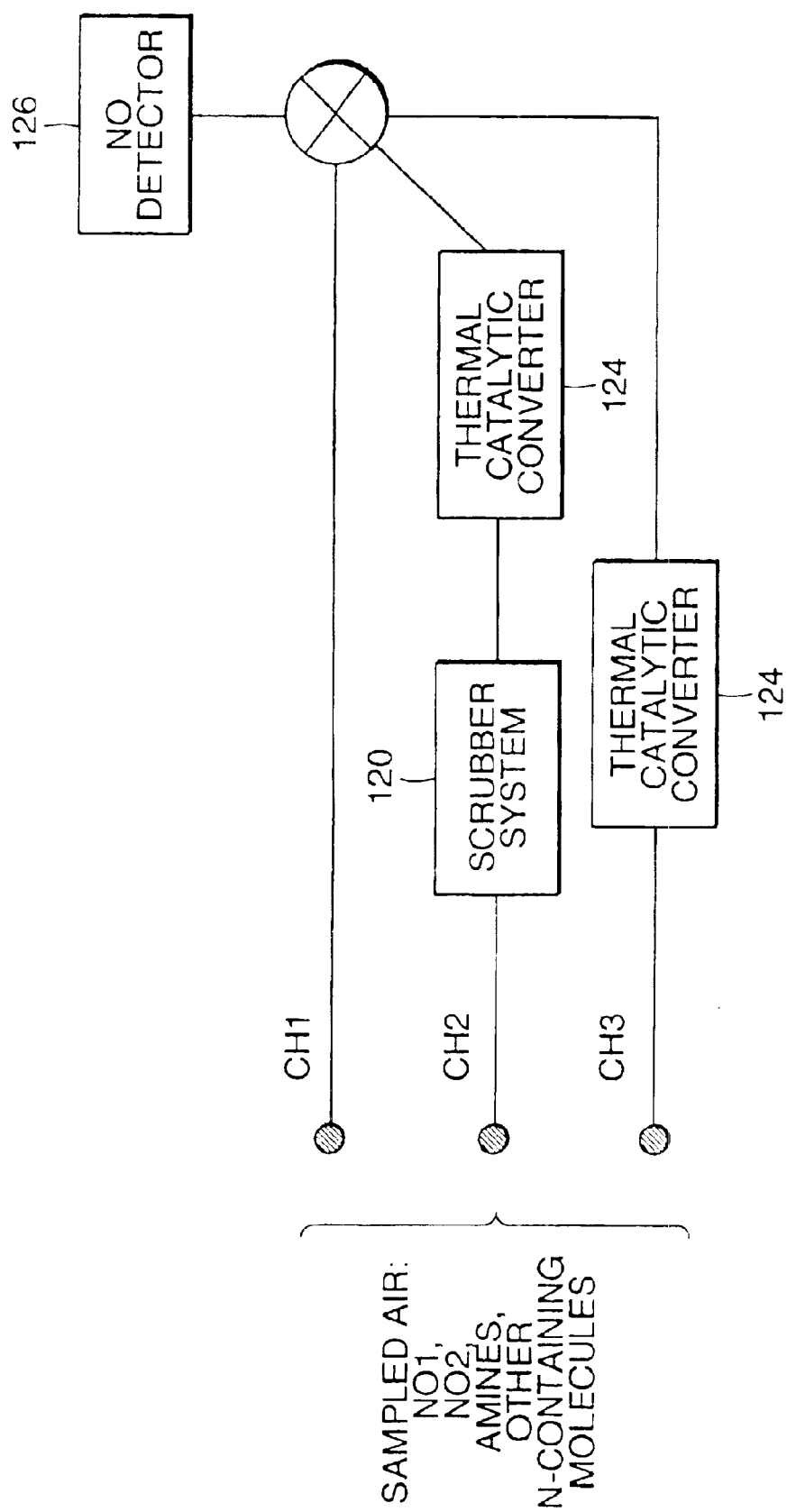
FIG. 8E is a schematic view of a detection system that includes three separate sample channels coupled to an NO detector.

Additional channels may be used to provide further analysis of the components of the sampled gas. For example, referring to FIG. 8E, three channels (CH1, CH2 and CH3) may be used to determine the component concentrations of NO, $NO_2$ and other non-basic nitrogen-containing compounds which are convertible to NO, and the total basic nitrogen compounds in a gas sample. The following discussion focuses on the various classes of nitrogen-containing compounds in the sampled gas. NO, $NO_2$, basic nitrogen compounds, and other N-containing compounds reach the NO detector through CH1; and the NO detector produces a signal representative of the NO concentration in the sampled gas. NO (including NO converted from $NO_2$ and other convertible N-containing molecules) and non-convertible N-containing molecules reach the NO detector through CH2; and the difference between the detector signals for CH1 and CH2 provides a measure of the concentration of $NO_2$ and other non-basic, nitrogen-containing compounds which are convertible to NO in the sampled gas. NO (including NO converted from $NO_2$, basic nitrogen compounds and other convertible N-containing molecules) and non-convertible N-containing molecules reach the NO detector through CH3; and the difference between the detector signals for CH2 and CH3 provides a measure of the total basic-nitrogen-compounds concentration in the sampled gas.

In some implementations, variations that occur in the ambient NO and $NO_2$ concentrations may affect the accuracy of the total basic-nitrogen-compound concentration measurement. In such cases where the disturbance warrants, an algorithm is used to minimize the effects of such fluctuations by calculating the total basic-nitrogen-compound concentration based on a moving average for NO concentrations from channel A and channel B. For example, each NO concentration measurement is added to the previous consecutive measurements and divided by the total number of measurements made at that point in time. This moving average calculation may be represented by the following algorithm:

Moving NO Average=(X1+X2+. . . +Xn)/n, where X equals the NO concentration at a given time and n equals the total number of NO measurements made. The moving average calculation may be reset periodically to avoid the weighting of out-of-date measurements. In another algorithm, a selected number of values are added together to provide an initial average value and thereafter the oldest value is dropped from the average as the newest measured valve is added to it.

As shown in FIGS. 8A and 8B, control system 130 (e.g., a computer), in addition to collecting and analyzing data received from chemiluminescence detector 126, controls selection valve 114, valve 122 (or valves 122a and 122b, as shown in FIG. 8C), and scrubber-system valves 125, 125' and 125". Selection valve 114 is controlled by control system 130 to channel samples from multiple sampling ports 112 into the conversion module 6 in a selected order. Valve 122 is controlled to switch between channel A and channel B on the basis of settling times (i.e., the time required for the measured NO value to reach equilibrium following a shift). Preferably, multiple switching cycles are employed for a given sample line and the measurements are averaged, or a running average is employed, to produce a reliable measure of total basic nitrogen compounds, as has been described.

Figure 9:
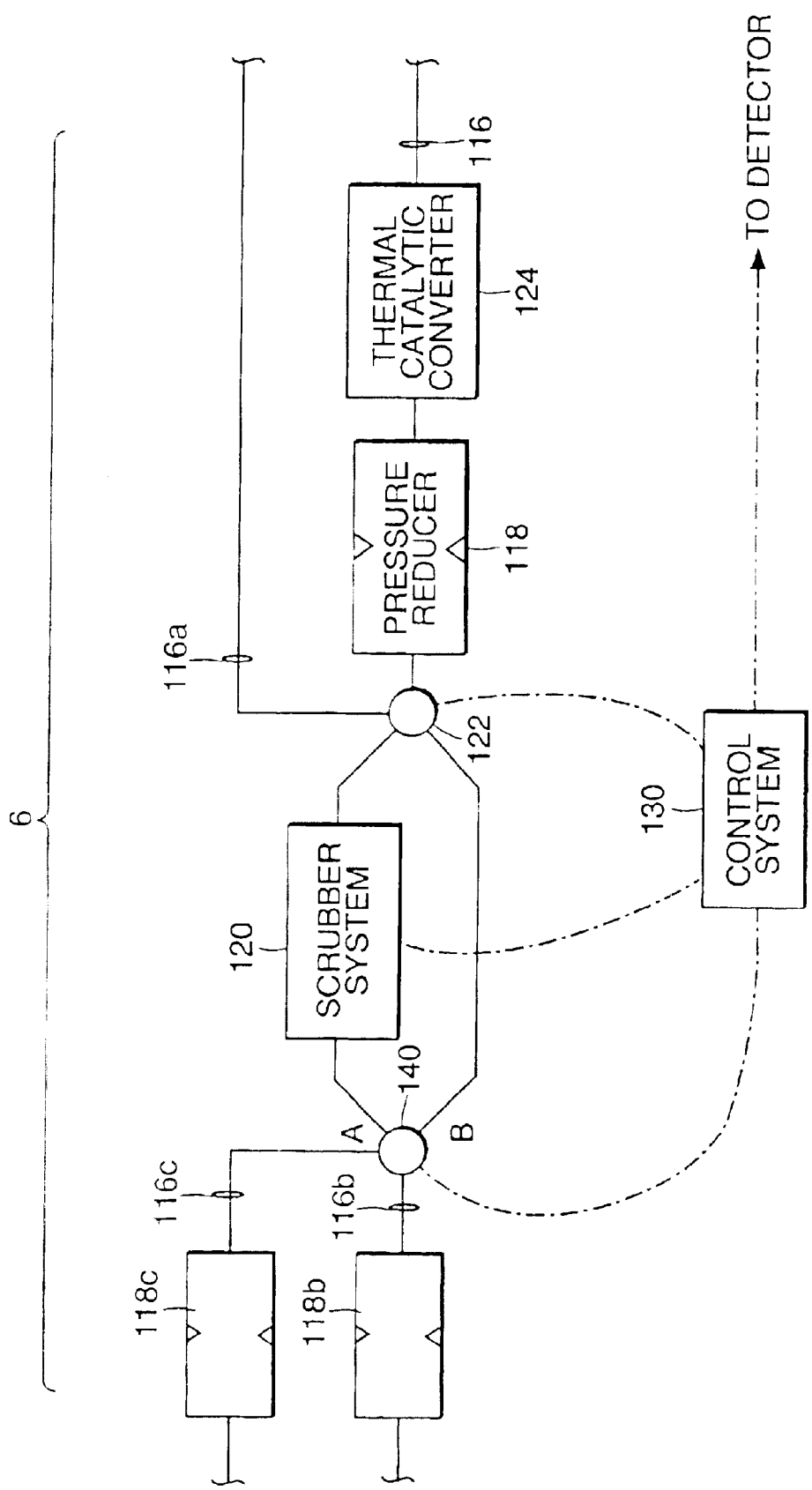
FIG. 9 is a schematic view of a sample delivery train similar to that of FIG. 8A in which an isolation valve is located upstream from a scrubber system.

Referring to FIG. 9, in another embodiment, conversion module 6 employs an additional valve 140 at the branching point of channels A and B. Valve 140, in conjunction with valve 122, isolates basic-nitrogen-compound scrubber system 120 and thus prevents the possibility of back-flow diffusion. The amount of sample that is directed by valve 140 to channel A and channel B is controlled by control system 130. In this embodiment, valve 122 is also connected to the vacuum pump by an auxiliary conduit 116a (which, again, is connected, in parallel with sample line 116, to a common vacuum pump) to draw gas through the non-selected channel so that substantially continuous flow conditions are maintained through both channels A and B at all times. Valve 140 is also connected to sample lines 116b and 116c, which are connected, in parallel, upstream from channels A and B. Sample lines 116b and 116c include respective pressure reducers 118b and 118c, which restrict the flow of sample gas to different degrees. When the sample gas is flowing through channel B, valve 140 selects the sample line with the more-restrictive pressure reducer (in this example, sample line 116c) as the source of that gas. The resistance of the more-restrictive pressure reducer is selected to offset the inherent flow restriction generated by the scrubber system 120. While channel B is selected, valve 140 connects sample line 116b, which has the less-restrictive pressure reducer, to supply a flow of gas sample through channel A and on through auxiliary sample line 116a.

Figure 10:
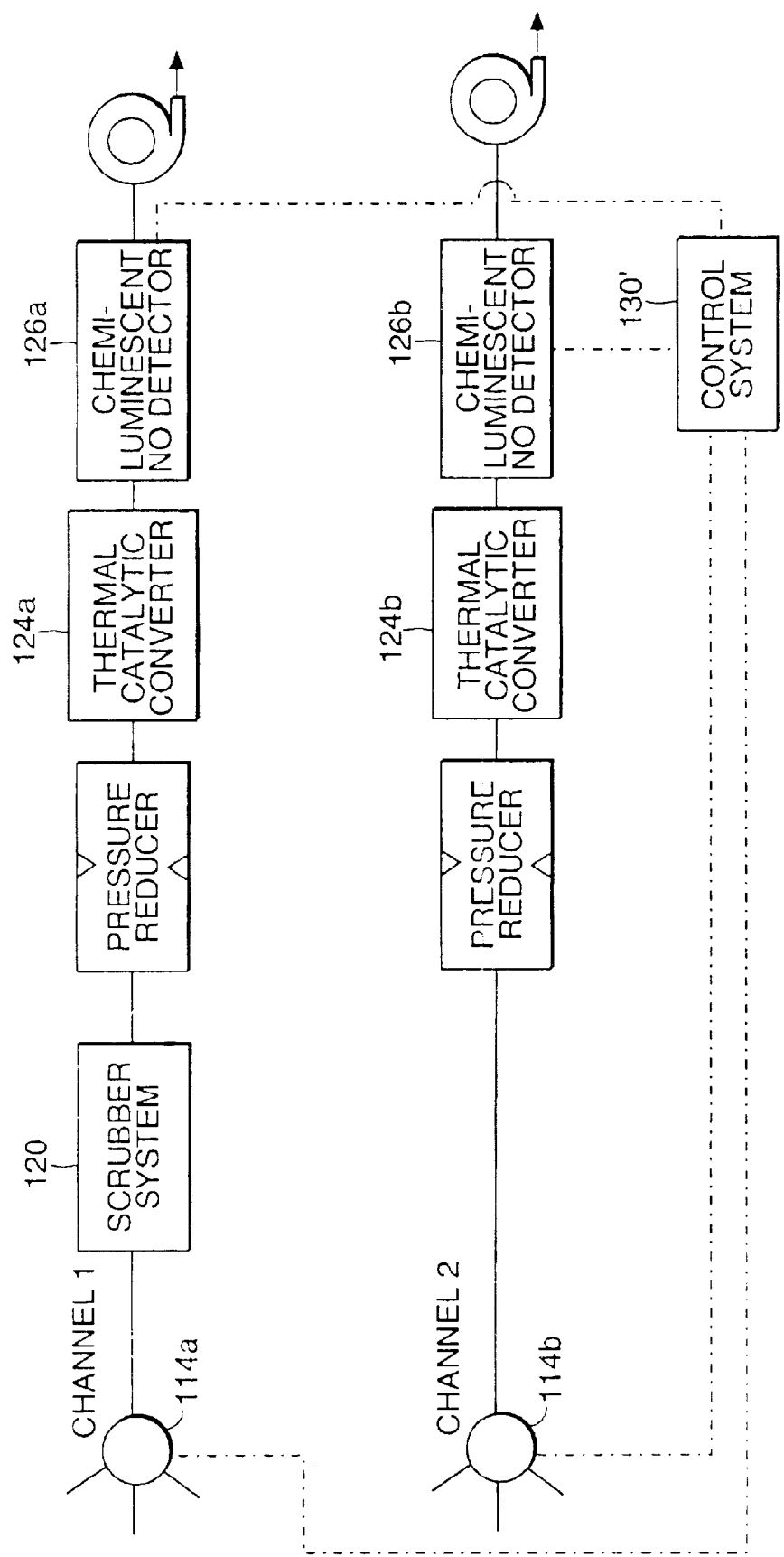
FIG. 10 is a view similar to FIG. 8A of a system implemented to be immune to variations in NO and other interferents at the sampling site.

Referring to FIG. 10, in another embodiment, a separate and distinct channel for producing a reference of zero air is operated parallel with another channel for determining the total basic-nitrogen-compound concentration. Sampling point selection valves 114a and 114b, for channels 1 and 2, may be gauged and arranged to simultaneously sample the same location. Channel 1 produces a reference of zero air by directing a sample to basic-nitrogen-compound scrubber system 120 and then to a thermal catalytic converter 124a and chemiluminescence detection device 126a. At the same time, channel 2 directs a sample to a thermal catalytic converter 124b and a chemiluminescence detection device 126b. The NO measurements from channel 1 and 2 are made simultaneously and then compared. This embodiment eliminates the effect of fluctuations in ambient NO and $NO_2$ concentrations by determining the actual NO and $NO_2$ concentration at the same time as the total NO response is being measured.

Control system 130' calculates the total basic-nitrogen-compound concentration based on the differences between the two readings from the detectors 126a, 126b. A calibration system (not shown) is employed to compatibly zero the instruments (e.g., to accommodate variations in the converters and detection devices) so that they can operate together. A correction factor based upon, e.g., computer look up of an experience table, can be employed for calibration purposes. A calibration routine can be conducted periodically, and drift trends can be measured and stored to create a dynamic correction algorithm.

This arrangement eliminates the possibility of noise from variations in ambient NO and $NO_2$ concentrations because the instantaneous value of the NO and $NO_2$ concentration is always known and does not change during a calculation cycle. This system, in effect, reduces the time between ambient NO and $NO_2$ measurements to zero, which solves the fundamental problem of fluctuations in NO and $NO_2$ concentrations during a single calculation cycle.

The various embodiments may be implemented in a number of useful ways. The parameters of the basic-nitrogen-compound scrubbers are selected to remove only those basic nitrogen compounds that affect a given process. In one advantageous example, beds of photoresist-coated beads are used as the scrubbers, the photoresist material being selected to correspond to the photoresist material being employed in the process being monitored. Thus, the scrubbers remove those basic nitrogen compounds to which the photoresist process is peculiarly sensitive. In an important case, the scrubbers used in the detection systems of FIGS. 8–10 are constructed and arranged to select construction materials for use in a basic-nitrogen-compound-sensitive process (e.g., chemically-amplified photoresist process). In another important case, the detection system of FIGS. 8–10 is connected to monitor the performance of a basic-nitrogen-compound gas filter system used to filter gas in a DUV stepper, scanner or coat/develop track. In another important case, the detection system of FIGS. 8–10 is connected to monitor the total basic-nitrogen-compound concentration inside a DUV stepper, scanner, or coat/develop track. In another important case, the detection system of FIGS. 8–10 is connected to monitor cleanroom concentration of total basic-nitrogen-compound concentration inside a DUV stepper, scanner, or coat/develop track.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A continuous-operation scrubber system to remove contaminants in a gas in a semiconductor processing tool comprising:
   a semiconductor processing tool;
   a pair of channels connected in parallel to a supply line of the semiconductor processing tool;
   a pair of scrubbers, each scrubber being coupled with a respective one of the pair of channels, such that each of the scrubbers removes a gas contaminant from the respective channel to deliver a scrubbed gas through the supply line to the semiconductor processing tool; and
   a purge system coupled with each scrubber for purging the removed gas contaminant from each scrubber.

2. The continuous-operation scrubber system of claim 1 further comprising a control system for directing a flow of gas through the channels.

3. The system of claim 1 wherein the purge system is coupled to at least one of the scrubbers for purging reversibly-bound basic nitrogen compounds from the scrubber.

4. The system of claim 1 wherein at least one of the scrubbers includes a cation exchange medium.

5. The system of claim 1 further comprising a converter and a flow controller that selectively controls which of the scrubbing channels the gas can flow through to the converter.

6. The system of claim 5 further comprising a detector wherein the flow controller is governed by a control system that is programmed to transfer the flow of a reference gas reaching the detector from a scrubbing channel with a contaminated scrubber to a scrubbing channel with a purged scrubber and to then direct a purge gas through the contaminated scrubber.

7. The system of claim 6 wherein the control system is programmed to transfer the flow of the reference gas away from one of the scrubbing channels and to purge the scrubber of that scrubbing channel before a weak-base nitrogen compound can penetrate through the scrubber.

8. The system of claim 7 further comprising a primary channel wherein the control system is programmed to alternately transfer the flow of a gas between the primary channel and one of the scrubbing channels.

9. The system of claim 1 further comprising a detector and a pressure reducer located between the detector and the scrubbers.

10. A method for continuously scrubbing a gas in a semiconductor processing tool comprising the steps of:
    delivering a gas to a scrubber system for a semiconductor processing tool including a first scrubber and a second scrubber connected in parallel;
    directing the gas through the first scrubber;
    purging the first scrubber while directing the gas through the second scrubber; and
    purging the second scrubber while directing the gas through the first scrubber, the scrubbed gas from the first scrubber and the second scrubber being delivered to a semiconductor processing tool.

11. The method of claim 10 wherein flow of the gas alternates between passing through the first scrubber and passing through the second scrubber.

12. The method of claim 10 further comprising the steps of:
    passing a first reference gas through the first scrubber to remove basic nitrogen compounds from a first reference gas; and
    passing a second reference gas through a second scrubber to remove basic nitrogen compounds from the second reference gas.

13. The method of claim 10 further comprising purging the first scrubber to remove reversibly-bound basic nitrogen compounds while passing a second reference gas through the second scrubber.

14. The method of claim 10 further comprising passing a first reference gas and a second reference gas through a converter which converts gaseous nitrogen compounds in first and second reference gases into an indicator gas after the first reference gas passes through the first scrubber and the second reference gas passes through the second scrubber.

15. The method of claim 14 further comprising directing the first and second reference gases to a detector which detects a concentration of the indicator gas in the first or second reference gas after the said reference gas is passed through the converter.

16. The method of claim 15 further comprising passing a target gas through the converter which converts gaseous nitrogen compounds in the target gas into the indicator gas; and
    passing the target gas through the detector which detects the concentration of the indicator gas in the target gas after the target gas passes through the converter.

17. The method of claim 16 further comprising determining a total basic-nitrogen-compound contamination concentration by comparing a detected concentration of the indicator gas in the target gas with a detected concentration of the indicator gas in the reference gas.

18. The method of claim 10 further comprising alternately detecting a concentration of an indicator gas in a reference gas flowing through the first scrubber and a concentration of the indicator gas in a reference gas flowing through the second scrubber.

19. The method of claim 10 further comprising the step of alternately purging the first and second scrubbers while maintaining flow of the gas to a converter and to a detector.

20. The method of claim 10 further comprising providing a detector and a processor connected to the detector.

* * * * *